US012691221B2

(12) United States Patent
Mazlish

(10) Patent No.: US 12,691,221 B2
(45) Date of Patent: Jul. 28, 2026

(54) DISCRETIONARY INSULIN DELIVERY SYSTEMS AND METHODS

(71) Applicant: Insulet Corporation, Acton, MA (US)

(72) Inventor: Bryan Mazlish, Palo Alto, CA (US)

(73) Assignee: Insulet Corporation, Acton, MA (US)

( * ) Notice: Subject to any disclaimer, the term of this patent is extended or adjusted under 35 U.S.C. 154(b) by 888 days.

(21) Appl. No.: 16/789,162

(22) Filed: Feb. 12, 2020

(65) Prior Publication Data

US 2020/0179602 A1 Jun. 11, 2020

Related U.S. Application Data

(63) Continuation of application No. 14/254,684, filed on Apr. 16, 2014, now abandoned.

(Continued)

(51) Int. Cl.
*A61B 5/00* (2006.01)
*A61B 5/145* (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC ............... A61M 31/00; A61M 31/002; A61M 2230/201; A61M 2005/14208;
(Continued)

(56) References Cited

U.S. PATENT DOCUMENTS 303,013 A 8/1884 Petez
445,545 A 2/1891 Crane
(Continued)

FOREIGN PATENT DOCUMENTS

AU 2015200834 A1 3/2015
CA 1040271 A 10/1978
(Continued)

OTHER PUBLICATIONS

US 5,954,699 A, 09/1999, Jost et al. (withdrawn)
(Continued)

Primary Examiner — Michael J Tsai
Assistant Examiner — William R Frehe
(74) *Attorney, Agent, or Firm* — TraskBritt

(57) ABSTRACT

A method of facilitating delivery of a discretionary dose of insulin to a user includes: enabling the user or a caregiver to specify, via a computer-based user interface, parameters associated with a discretionary delivery of insulin that may be delivered to the user; subsequently receiving data that represents the user's glucose level during a period of time associated with the discretionary delivery; automatically determining, with a computer-based processor, based on the received data, if, when and how much discretionary insulin should be delivered to the user during the period of time associated with the discretionary delivery; delivering insulin to the user during the period of time associated with the discretionary delivery according to the automatic determination; and delivering insulin to the user with the insulin delivery device according to a non-discretionary insulin delivery schedule unless a discretionary insulin delivery mode has been triggered.

6 Claims, 12 Drawing Sheets

Related U.S. Application Data

(60) Provisional application No. 61/908,981, filed on Nov. 26, 2013, provisional application No. 61/812,452, filed on Apr. 16, 2013.

(51) Int. Cl.
*A61M 5/142* (2006.01)
*A61M 5/172* (2006.01)
*G16H 20/17* (2018.01)

(52) U.S. Cl.
CPC ........ *A61M 5/14244* (2013.01); *G16H 20/17* (2018.01); *A61M 2005/14208* (2013.01); *A61M 2205/18* (2013.01); *A61M 2205/3553* (2013.01); *A61M 2205/3561* (2013.01); *A61M 2205/3584* (2013.01); *A61M 2205/3592* (2013.01); *A61M 2209/01* (2013.01); *A61M 2230/201* (2013.01)

(58) Field of Classification Search
CPC .......... A61M 2005/1726; A61M 5/142; A61M 5/1723; A61M 5/14244
See application file for complete search history.

(56) References Cited

U.S. PATENT DOCUMENTS

| | | |
|---|---|---|
| 588,583 A | 8/1897 | Crane |
| 1,441,508 A | 1/1923 | Marius et al. |
| 2,283,925 A | 5/1942 | Harvey |
| 2,797,149 A | 6/1957 | Skeggs |
| 2,886,529 A | 5/1959 | Guillaud |
| 3,413,573 A | 11/1968 | Nathanson et al. |
| 3,574,114 A | 4/1971 | Monforte |
| 3,614,554 A | 10/1971 | Shield et al. |
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,885,662 A | 5/1975 | Schaefer |
| 3,963,380 A | 6/1976 | Thomas et al. |
| 3,983,077 A | 9/1976 | Fuller et al. |
| 4,055,175 A | 10/1977 | Clemens et al. |
| 4,108,177 A | 8/1978 | Pistor |
| 4,146,029 A | 3/1979 | Ellinwood, Jr. |
| 4,151,845 A | 5/1979 | Clemens |
| 4,245,634 A | 1/1981 | Albisser et al. |
| 4,268,150 A | 5/1981 | Chen |
| 4,295,176 A | 10/1981 | Wittwer |
| 4,313,439 A | 2/1982 | Babb et al. |
| 4,368,980 A | 1/1983 | Aldred et al. |
| 4,373,527 A | 2/1983 | Fischell |
| 4,400,683 A | 8/1983 | Eda et al. |
| 4,403,984 A | 9/1983 | Ash et al. |
| 4,424,720 A | 1/1984 | Bucchianeri |
| 4,435,173 A | 3/1984 | Siposs et al. |
| 4,464,170 A | 8/1984 | Clemens et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,523,170 A | 6/1985 | Huth, III |
| 4,526,568 A | 7/1985 | Clemens et al. |
| 4,526,569 A | 7/1985 | Bernardi |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,562,751 A | 1/1986 | Nason et al. |
| 4,573,968 A | 3/1986 | Parker |
| 4,585,439 A | 4/1986 | Michel |
| 4,601,707 A | 7/1986 | Albisser et al. |
| 4,624,661 A | 11/1986 | Arimond |
| 4,633,878 A | 1/1987 | Bombardieri |
| 4,634,427 A | 1/1987 | Hannula et al. |
| 4,646,038 A | 2/1987 | Wanat |
| 4,657,529 A | 4/1987 | Prince et al. |
| 4,678,408 A | 7/1987 | Nason et al. |
| 4,684,368 A | 8/1987 | Kenyon |
| 4,685,903 A | 8/1987 | Cable et al. |
| 4,731,726 A | 3/1988 | Allen, III |
| 4,743,243 A | 5/1988 | Vaillancourt |
| 4,755,169 A | 7/1988 | Sarnoff et al. |
| 4,755,173 A | 7/1988 | Konopka et al. |
| 4,759,120 A | 7/1988 | Bernstein |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,859,492 A | 8/1989 | Rogers et al. |
| 4,880,770 A | 11/1989 | Mir et al. |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,944,659 A | 7/1990 | Labbe et al. |
| 4,967,201 A | 10/1990 | Rich, III |
| 4,969,874 A | 11/1990 | Michel et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,007,458 A | 4/1991 | Marcus et al. |
| 5,061,424 A | 10/1991 | Karimi et al. |
| 5,062,841 A | 11/1991 | Siegel |
| 5,084,749 A | 1/1992 | Losee et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,130,675 A | 7/1992 | Sugawara |
| 5,134,079 A | 7/1992 | Cusack et al. |
| 5,139,999 A | 8/1992 | Gordon et al. |
| 5,153,827 A | 10/1992 | Coutre et al. |
| 5,154,973 A | 10/1992 | Imagawa et al. |
| 5,165,406 A | 11/1992 | Wong |
| 5,176,662 A | 1/1993 | Bartholomew et al. |
| 5,178,609 A | 1/1993 | Ishikawa |
| 5,189,609 A | 2/1993 | Tivig et al. |
| 5,198,824 A | 3/1993 | Poradish |
| 5,205,819 A | 4/1993 | Ross et al. |
| 5,207,642 A | 5/1993 | Orkin et al. |
| 5,213,483 A | 5/1993 | Flaherty et al. |
| 5,217,754 A | 6/1993 | Santiago-Aviles et al. |
| 5,219,377 A | 6/1993 | Poradish |
| 5,232,439 A | 8/1993 | Campbell et al. |
| 5,237,993 A | 8/1993 | Skrabal |
| 5,244,463 A | 9/1993 | Cordner et al. |
| 5,254,096 A | 10/1993 | Rondelet et al. |
| 5,257,980 A | 11/1993 | Van et al. |
| 5,261,882 A | 11/1993 | Sealfon |
| 5,263,198 A | 11/1993 | Geddes et al. |
| 5,272,485 A | 12/1993 | Mason et al. |
| 5,273,517 A | 12/1993 | Barone et al. |
| 5,281,202 A | 1/1994 | Weber et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,346,476 A | 9/1994 | Elson |
| 5,364,342 A | 11/1994 | Beuchat et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky et al. |
| 5,403,797 A | 4/1995 | Ohtani et al. |
| 5,411,889 A | 5/1995 | Hoots et al. |
| 5,421,812 A | 6/1995 | Langley et al. |
| 5,427,988 A | 6/1995 | Sengupta et al. |
| 5,433,710 A | 7/1995 | Vanantwerp et al. |

(56)        References Cited

U.S. PATENT DOCUMENTS

| | | | |
|---|---|---|---|
| 5,456,945 | A | 10/1995 | McMillan et al. |
| 5,468,727 | A | 11/1995 | Phillips et al. |
| 5,478,610 | A | 12/1995 | Desu et al. |
| 5,505,709 | A | 4/1996 | Funderburk et al. |
| 5,505,828 | A | 4/1996 | Wong et al. |
| 5,507,288 | A | 4/1996 | Boecker et al. |
| 5,513,382 | A | 4/1996 | Agahi-Kesheh et al. |
| 5,533,389 | A | 7/1996 | Kamen et al. |
| 5,535,445 | A | 7/1996 | Gunton |
| 5,540,772 | A | 7/1996 | McMillan et al. |
| 5,543,773 | A | 8/1996 | Evans et al. |
| 5,558,640 | A | 9/1996 | Pfeiler et al. |
| 5,569,186 | A | 10/1996 | Lord et al. |
| 5,582,593 | A | 12/1996 | Hultman |
| 5,584,053 | A | 12/1996 | Kommrusch et al. |
| 5,584,813 | A | 12/1996 | Livingston et al. |
| 5,590,387 | A | 12/1996 | Schmidt et al. |
| 5,609,572 | A | 3/1997 | Lang |
| 5,614,252 | A | 3/1997 | Mcmillan et al. |
| 5,625,365 | A | 4/1997 | Tom et al. |
| 5,635,433 | A | 6/1997 | Sengupta |
| 5,637,095 | A | 6/1997 | Nason et al. |
| 5,665,065 | A | 9/1997 | Colman et al. |
| 5,665,070 | A | 9/1997 | McPhee |
| 5,678,539 | A | 10/1997 | Schubert et al. |
| 5,685,844 | A | 11/1997 | Marttila |
| 5,685,859 | A | 11/1997 | Kornerup |
| 5,693,018 | A | 12/1997 | Kriesel et al. |
| 5,697,899 | A | 12/1997 | Hillman et al. |
| 5,700,695 | A | 12/1997 | Yassinzadeh et al. |
| 5,703,364 | A | 12/1997 | Rosenthal |
| 5,707,459 | A | 1/1998 | Itoyama et al. |
| 5,707,715 | A | 1/1998 | Derochemont et al. |
| 5,713,875 | A | 2/1998 | Tanner, II |
| 5,714,123 | A | 2/1998 | Sohrab |
| 5,716,343 | A | 2/1998 | Kriesel et al. |
| 5,722,397 | A | 3/1998 | Eppstein |
| 5,741,228 | A | 4/1998 | Lambrecht et al. |
| 5,746,217 | A | 5/1998 | Erickson et al. |
| 5,747,350 | A | 5/1998 | Sattler |
| 5,747,870 | A | 5/1998 | Pedder |
| 5,748,827 | A | 5/1998 | Holl et al. |
| 5,755,682 | A | 5/1998 | Knudson et al. |
| 5,758,643 | A | 6/1998 | Wong et al. |
| 5,759,923 | A | 6/1998 | McMillan et al. |
| 5,764,189 | A | 6/1998 | Lohninger |
| 5,771,567 | A | 6/1998 | Pierce et al. |
| 5,776,103 | A | 7/1998 | Kriesel et al. |
| 5,779,676 | A | 7/1998 | Kriesel et al. |
| 5,785,688 | A | 7/1998 | Joshi et al. |
| 5,797,881 | A | 8/1998 | Gadot |
| 5,800,397 | A | 9/1998 | Wilson et al. |
| 5,800,405 | A | 9/1998 | McPhee |
| 5,800,420 | A | 9/1998 | Gross et al. |
| 5,801,057 | A | 9/1998 | Smart et al. |
| 5,804,048 | A | 9/1998 | Wong et al. |
| 5,807,075 | A | 9/1998 | Jacobsen et al. |
| 5,817,007 | A | 10/1998 | Fodgaard et al. |
| 5,820,622 | A | 10/1998 | Gross et al. |
| 5,822,715 | A | 10/1998 | Worthington et al. |
| 5,823,951 | A | 10/1998 | Messerschmidt |
| 5,839,467 | A | 11/1998 | Saaski et al. |
| 5,840,020 | A | 11/1998 | Heinonen et al. |
| D403,313 | S | 12/1998 | Peppel |
| 5,848,991 | A | 12/1998 | Gross et al. |
| 5,851,197 | A | 12/1998 | Marano et al. |
| 5,854,608 | A | 12/1998 | Leisten |
| 5,858,005 | A | 1/1999 | Kriesel |
| 5,858,239 | A | 1/1999 | Kenley et al. |
| 5,859,621 | A | 1/1999 | Leisten |
| 5,865,806 | A | 2/1999 | Howell |
| 5,871,470 | A | 2/1999 | Mcwha |
| 5,879,310 | A | 3/1999 | Sopp et al. |
| 5,889,459 | A | 3/1999 | Hattori et al. |
| 5,891,097 | A | 4/1999 | Saito et al. |
| 5,892,489 | A | 4/1999 | Kanba et al. |
| 5,897,530 | A | 4/1999 | Jackson |
| 5,902,253 | A | 5/1999 | Pfeiffer et al. |
| 5,903,421 | A | 5/1999 | Furutani et al. |
| 5,906,597 | A | 5/1999 | McPhee |
| 5,911,716 | A | 6/1999 | Rake et al. |
| 5,919,167 | A | 7/1999 | Mulhauser et al. |
| 5,931,814 | A | 8/1999 | Alex et al. |
| 5,932,175 | A | 8/1999 | Knute et al. |
| 5,933,121 | A | 8/1999 | Rainhart et al. |
| 5,935,099 | A | 8/1999 | Peterson et al. |
| 5,945,963 | A | 8/1999 | Leisten |
| 5,947,911 | A | 9/1999 | Wong et al. |
| 5,957,890 | A | 9/1999 | Mann et al. |
| 5,961,492 | A | 10/1999 | Kriesel et al. |
| 5,965,848 | A | 10/1999 | Altschul et al. |
| 5,971,922 | A | 10/1999 | Arita et al. |
| 5,971,941 | A | 10/1999 | Simons et al. |
| 5,993,423 | A | 11/1999 | Choi |
| 5,997,501 | A | 12/1999 | Gross et al. |
| 6,005,151 | A | 12/1999 | Herrmann et al. |
| 6,017,318 | A | 1/2000 | Gauthier et al. |
| 6,019,747 | A | 2/2000 | McPhee |
| 6,023,251 | A | 2/2000 | Koo et al. |
| 6,024,539 | A | 2/2000 | Blomquist |
| 6,027,826 | A | 2/2000 | Derochemont et al. |
| 6,028,568 | A | 2/2000 | Asakura et al. |
| 6,031,445 | A | 2/2000 | Marty et al. |
| 6,032,059 | A | 2/2000 | Henning et al. |
| 6,036,924 | A | 3/2000 | Simons et al. |
| 6,040,578 | A | 3/2000 | Malin et al. |
| 6,040,805 | A | 3/2000 | Huynh et al. |
| 6,046,707 | A | 4/2000 | Gaughan et al. |
| 6,049,727 | A | 4/2000 | Crothall |
| 6,050,978 | A | 4/2000 | Orr et al. |
| 6,052,040 | A | 4/2000 | Hino |
| 6,058,934 | A | 5/2000 | Sullivan |
| 6,066,103 | A | 5/2000 | Duchon et al. |
| 6,071,292 | A | 6/2000 | Makower et al. |
| 6,072,180 | A | 6/2000 | Kramer et al. |
| 6,077,055 | A | 6/2000 | Vilks |
| 6,081,786 | A | 6/2000 | Barry et al. |
| 6,090,092 | A | 7/2000 | Fowles et al. |
| 6,101,406 | A | 8/2000 | Hacker et al. |
| 6,102,872 | A | 8/2000 | Doneen et al. |
| 6,111,544 | A | 8/2000 | Dakeya et al. |
| 6,115,673 | A | 9/2000 | Malin et al. |
| 6,123,827 | A | 9/2000 | Wong et al. |
| 6,124,134 | A | 9/2000 | Stark |
| 6,126,637 | A | 10/2000 | Kriesel et al. |
| 6,128,519 | A | 10/2000 | Say |
| 6,142,939 | A | 11/2000 | Eppstein et al. |
| 6,143,164 | A | 11/2000 | Heller et al. |
| 6,143,432 | A | 11/2000 | De et al. |
| 6,154,176 | A | 11/2000 | Fathy et al. |
| 6,157,041 | A | 12/2000 | Thomas et al. |
| 6,161,028 | A | 12/2000 | Braig et al. |
| 6,162,639 | A | 12/2000 | Douglas |
| 6,174,300 | B1 | 1/2001 | Kriesel et al. |
| 6,176,004 | B1 | 1/2001 | Rainhart et al. |
| 6,181,297 | B1 | 1/2001 | Leisten |
| 6,188,368 | B1 | 2/2001 | Koriyama et al. |
| 6,190,359 | B1 | 2/2001 | Heruth |
| 6,195,049 | B1 | 2/2001 | Kim et al. |
| 6,196,046 | B1 | 3/2001 | Braig et al. |
| 6,200,287 | B1 | 3/2001 | Keller et al. |
| 6,200,293 | B1 | 3/2001 | Kriesel et al. |
| 6,200,338 | B1 | 3/2001 | Solomon et al. |
| 6,204,203 | B1 | 3/2001 | Narwankar et al. |
| 6,208,843 | B1 | 3/2001 | Huang et al. |
| 6,214,629 | B1 | 4/2001 | Freitag et al. |
| 6,222,489 | B1 | 4/2001 | Tsuru et al. |
| 6,226,082 | B1 | 5/2001 | Roe |
| 6,244,776 | B1 | 6/2001 | Wiley |
| 6,261,065 | B1 | 7/2001 | Nayak et al. |
| 6,262,798 | B1 | 7/2001 | Shepherd et al. |
| 6,266,020 | B1 | 7/2001 | Chang |
| 6,270,455 | B1 | 8/2001 | Brown |
| 6,271,045 | B1 | 8/2001 | Douglas et al. |

(56) References Cited

U.S. PATENT DOCUMENTS

| | | |
|---|---|---|
| 6,280,381 B1 | 8/2001 | Malin et al. |
| 6,285,448 B1 | 9/2001 | Kuenstner |
| 6,300,894 B1 | 10/2001 | Lynch et al. |
| 6,309,370 B1 | 10/2001 | Haim et al. |
| 6,312,888 B1 | 11/2001 | Wong et al. |
| 6,320,547 B1 | 11/2001 | Fathy et al. |
| 6,323,549 B1 | 11/2001 | Derochemont et al. |
| 6,334,851 B1 | 1/2002 | Hayes et al. |
| 6,363,609 B1 | 4/2002 | Pickren |
| 6,375,627 B1 | 4/2002 | Mauze et al. |
| 6,375,638 B2 | 4/2002 | Nason et al. |
| 6,379,301 B1 | 4/2002 | Worthington et al. |
| 6,402,689 B1 | 6/2002 | Scarantino et al. |
| 6,413,244 B1 | 7/2002 | Bestetti et al. |
| 6,470,279 B1 | 10/2002 | Samsoondar |
| 6,474,219 B2 | 11/2002 | Klitmose et al. |
| 6,475,196 B1 | 11/2002 | Vachon |
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,492,949 B1 | 12/2002 | Breglia et al. |
| 6,496,149 B1 | 12/2002 | Birnbaum et al. |
| 6,501,415 B1 | 12/2002 | Mana et al. |
| 6,512,937 B2 | 1/2003 | Blank et al. |
| 6,520,936 B1 | 2/2003 | Mann |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,537,249 B2 | 3/2003 | Kriesell et al. |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |
| 6,546,268 B1 | 4/2003 | Ishikawa et al. |
| 6,546,269 B1 | 4/2003 | Kurnik |
| 6,552,693 B1 | 4/2003 | Leisten |
| 6,553,841 B1 | 4/2003 | Blouch |
| 6,554,798 B1 | 4/2003 | Mann et al. |
| 6,556,850 B1 | 4/2003 | Braig et al. |
| D474,778 S | 5/2003 | Barnes |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,115 B1 | 5/2003 | Barker et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,583,699 B2 | 6/2003 | Yokoyama |
| 6,595,919 B2 | 7/2003 | Berner et al. |
| 6,595,956 B1 | 7/2003 | Gross et al. |
| 6,611,419 B1 | 8/2003 | Chakravorty |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |
| 6,639,556 B2 | 10/2003 | Baba |
| 6,642,908 B2 | 11/2003 | Pleva et al. |
| 6,645,142 B2 | 11/2003 | Braig et al. |
| 6,650,303 B2 | 11/2003 | Kim et al. |
| 6,653,091 B1 | 11/2003 | Dunn et al. |
| 6,656,158 B2 | 12/2003 | Mahoney et al. |
| 6,662,030 B2 | 12/2003 | Khalil et al. |
| 6,669,663 B1 | 12/2003 | Thompson |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,686,406 B2 | 2/2004 | Tomomatsu et al. |
| 6,690,336 B1 | 2/2004 | Leisten et al. |
| 6,691,043 B2 | 2/2004 | Ribeiro, Jr. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,890 B2 | 5/2004 | Imanaka et al. |
| 6,740,059 B2 | 5/2004 | Flaherty |
| 6,740,072 B2 | 5/2004 | Starkweather et al. |
| 6,741,148 B2 | 5/2004 | Killen et al. |
| 6,742,249 B2 | 6/2004 | Derochemont et al. |
| 6,743,744 B1 | 6/2004 | Kim et al. |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,753,745 B2 | 6/2004 | Killen et al. |
| 6,753,814 B2 | 6/2004 | Killen et al. |
| 6,758,835 B2 | 7/2004 | Close et al. |
| 6,762,237 B2 | 7/2004 | Glatkowski et al. |
| 6,780,156 B2 | 8/2004 | Haueter et al. |
| 6,787,181 B2 | 9/2004 | Uchiyama et al. |
| 6,791,496 B1 | 9/2004 | Killen et al. |
| 6,810,290 B2 | 10/2004 | Lebel et al. |
| 6,826,031 B2 | 11/2004 | Nagai et al. |
| 6,830,623 B2 | 12/2004 | Hayashi et al. |
| 6,835,175 B1 | 12/2004 | Porumbescu |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,853,288 B2 | 2/2005 | Ahn et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,878,871 B2 | 4/2005 | Scher et al. |
| 6,883,778 B1 | 4/2005 | Newton et al. |
| 6,890,291 B2 | 5/2005 | Robinson et al. |
| 6,905,989 B2 | 6/2005 | Ellis et al. |
| 6,906,674 B2 | 6/2005 | McKinzie et al. |
| 6,914,566 B2 | 7/2005 | Beard |
| 6,919,119 B2 | 7/2005 | Kalkan et al. |
| 6,925,393 B1 | 8/2005 | Kalatz et al. |
| 6,928,298 B2 | 8/2005 | Furutani et al. |
| 6,936,029 B2 | 8/2005 | Mann et al. |
| 6,943,430 B2 | 9/2005 | Kwon |
| 6,943,731 B2 | 9/2005 | Killen et al. |
| 6,949,081 B1 | 9/2005 | Chance |
| 6,958,809 B2 | 10/2005 | Sterling et al. |
| 6,963,259 B2 | 11/2005 | Killen et al. |
| 6,989,891 B2 | 1/2006 | Braig et al. |
| 6,990,366 B2 | 1/2006 | Say et al. |
| 7,002,436 B2 | 2/2006 | Ma et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis et al. |
| 7,047,637 B2 | 5/2006 | Derochemont et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,116,949 B2 | 10/2006 | Irie et al. |
| 7,128,727 B2 | 10/2006 | Flaherty et al. |
| 7,137,694 B2 | 11/2006 | Ferran et al. |

(56) References Cited

U.S. PATENT DOCUMENTS

| | | | |
|---|---|---|---|
| 7,137,951 | B2 | 11/2006 | Pilarski |
| 7,139,593 | B2 | 11/2006 | Kavak et al. |
| 7,139,598 | B2 | 11/2006 | Hull et al. |
| 7,144,384 | B2 | 12/2006 | Gorman et al. |
| 7,160,272 | B1 | 1/2007 | Eyal et al. |
| 7,171,252 | B1 | 1/2007 | Scarantino et al. |
| 7,190,988 | B2 | 3/2007 | Say et al. |
| 7,204,823 | B2 | 4/2007 | Estes et al. |
| 7,230,316 | B2 | 6/2007 | Yamazaki et al. |
| 7,248,912 | B2 | 7/2007 | Gough et al. |
| 7,266,400 | B2 | 9/2007 | Fine et al. |
| 7,267,665 | B2 | 9/2007 | Steil et al. |
| 7,271,912 | B2 | 9/2007 | Sterling et al. |
| 7,278,983 | B2 | 10/2007 | Ireland et al. |
| 7,291,107 | B2 | 11/2007 | Hellwig et al. |
| 7,291,497 | B2 | 11/2007 | Holmes et al. |
| 7,291,782 | B2 | 11/2007 | Sager et al. |
| 7,303,549 | B2 | 12/2007 | Flaherty et al. |
| 7,303,622 | B2 | 12/2007 | Loch et al. |
| 7,303,922 | B2 | 12/2007 | Jeng et al. |
| 7,354,420 | B2 | 4/2008 | Steil et al. |
| 7,388,202 | B2 | 6/2008 | Sterling et al. |
| 7,402,153 | B2 | 7/2008 | Steil et al. |
| 7,404,796 | B2 | 7/2008 | Ginsberg |
| 7,405,698 | B2 | 7/2008 | De Rochemont |
| 7,429,255 | B2 | 9/2008 | Thompson |
| 7,460,130 | B2 | 12/2008 | Salganicoff |
| 7,481,787 | B2 | 1/2009 | Gable et al. |
| 7,491,187 | B2 | 2/2009 | Van et al. |
| 7,500,949 | B2 | 3/2009 | Gottlieb et al. |
| 7,509,156 | B2 | 3/2009 | Flanders |
| D590,415 | S | 4/2009 | Ball et al. |
| 7,522,124 | B2 | 4/2009 | Smith et al. |
| 7,547,281 | B2 | 6/2009 | Hayes et al. |
| 7,553,512 | B2 | 6/2009 | Kodas et al. |
| 7,564,887 | B2 | 7/2009 | Wang et al. |
| 7,569,030 | B2 | 8/2009 | Lebel et al. |
| 7,570,980 | B2 | 8/2009 | Ginsberg |
| 7,595,623 | B2 | 9/2009 | Bennett |
| 7,608,042 | B2 | 10/2009 | Goldberger et al. |
| 7,651,845 | B2 | 1/2010 | Doyle et al. |
| 7,652,901 | B2 | 1/2010 | Kirchmeier et al. |
| 7,680,529 | B2 | 3/2010 | Kroll |
| D614,634 | S | 4/2010 | Nilsen |
| 7,714,794 | B2 | 5/2010 | Tavassoli Hozouri |
| 7,734,323 | B2 | 6/2010 | Blomquist et al. |
| 7,763,917 | B2 | 7/2010 | De Rochemont |
| 7,766,829 | B2 | 8/2010 | Sloan et al. |
| 7,771,391 | B2 | 8/2010 | Carter |
| 7,785,258 | B2 | 8/2010 | Braig et al. |
| 7,806,854 | B2 | 10/2010 | Damiano et al. |
| 7,806,886 | B2 | 10/2010 | Kanderian et al. |
| 7,812,774 | B2 | 10/2010 | Friman et al. |
| 7,850,641 | B2 | 12/2010 | Lebel et al. |
| 7,918,825 | B2 | 4/2011 | O'Connor et al. |
| 7,920,998 | B2 | 4/2011 | Brown |
| 7,946,985 | B2 | 5/2011 | Mastrototaro et al. |
| 7,949,507 | B2 | 5/2011 | Brown |
| D640,269 | S | 6/2011 | Chen |
| 7,972,296 | B2 | 7/2011 | Braig et al. |
| 7,979,259 | B2 | 7/2011 | Brown |
| 8,066,805 | B2 | 11/2011 | Zuercher et al. |
| 8,069,690 | B2 | 12/2011 | Desantolo et al. |
| 8,114,489 | B2 | 2/2012 | Nemat-Nasser et al. |
| RE43,316 | E | 4/2012 | Brown et al. |
| 8,147,446 | B2 | 4/2012 | Yodfat et al. |
| 8,178,457 | B2 | 5/2012 | De Rochemont |
| 8,193,873 | B2 | 6/2012 | Kato et al. |
| 8,204,729 | B2 | 6/2012 | Sher |
| 8,206,296 | B2 | 6/2012 | Jennewine |
| 8,221,345 | B2 | 7/2012 | Blomquist |
| 8,251,907 | B2 | 8/2012 | Sterling et al. |
| 8,257,300 | B2 | 9/2012 | Budiman et al. |
| 8,265,726 | B2 | 9/2012 | Say et al. |
| 8,267,921 | B2 | 9/2012 | Yodfat et al. |
| 8,273,022 | B2 | 9/2012 | Say et al. |
| 8,298,184 | B2 | 10/2012 | Diperna et al. |
| 8,350,657 | B2 | 1/2013 | Derochemont |
| 8,354,294 | B2 | 1/2013 | De et al. |
| D677,685 | S | 3/2013 | Simmons et al. |
| 8,452,359 | B2 | 5/2013 | Rebec et al. |
| 8,467,980 | B2 | 6/2013 | Campbell et al. |
| 8,478,557 | B2 | 7/2013 | Hayter et al. |
| D688,686 | S | 8/2013 | Rhee et al. |
| 8,547,239 | B2 | 10/2013 | Peatfield et al. |
| D693,837 | S | 11/2013 | Bouchier |
| 8,593,819 | B2 | 11/2013 | De Rochemont |
| D695,757 | S | 12/2013 | Ray et al. |
| 8,622,988 | B2 | 1/2014 | Hayter |
| 8,715,839 | B2 | 5/2014 | De Rochemont |
| D710,879 | S | 8/2014 | Elston et al. |
| 8,810,394 | B2 | 8/2014 | Kalpin |
| D714,822 | S | 10/2014 | Capua et al. |
| D715,315 | S | 10/2014 | Wood |
| D715,815 | S | 10/2014 | Bortman et al. |
| D718,779 | S | 12/2014 | Hang et al. |
| D720,366 | S | 12/2014 | Hiltunen et al. |
| D720,765 | S | 1/2015 | Xie et al. |
| 8,939,935 | B2 | 1/2015 | O'Connor et al. |
| D726,760 | S | 4/2015 | Yokota et al. |
| D727,928 | S | 4/2015 | Allison et al. |
| D730,378 | S | 5/2015 | Xiong et al. |
| D733,175 | S | 6/2015 | Bae |
| 9,061,097 | B2 | 6/2015 | Holt et al. |
| D734,356 | S | 7/2015 | Xiong et al. |
| D736,811 | S | 8/2015 | Teichner et al. |
| D737,305 | S | 8/2015 | Scazafavo et al. |
| D737,831 | S | 9/2015 | Lee |
| D737,832 | S | 9/2015 | Lim et al. |
| D738,901 | S | 9/2015 | Amin |
| D740,301 | S | 10/2015 | Soegiono et al. |
| D740,308 | S | 10/2015 | Kim et al. |
| D740,311 | S | 10/2015 | Drozd et al. |
| D741,354 | S | 10/2015 | Lee et al. |
| D741,359 | S | 10/2015 | Ji-Hye et al. |
| 9,171,343 | B1 | 10/2015 | Fischell et al. |
| D743,431 | S | 11/2015 | Pal et al. |
| D743,991 | S | 11/2015 | Pal et al. |
| 9,180,224 | B2 | 11/2015 | Moseley et al. |
| 9,180,244 | B2 | 11/2015 | Anderson et al. |
| 9,192,716 | B2 | 11/2015 | Jugl et al. |
| D744,514 | S | 12/2015 | Shin et al. |
| D744,517 | S | 12/2015 | Pal et al. |
| D745,032 | S | 12/2015 | Pal et al. |
| D745,034 | S | 12/2015 | Pal et al. |
| D745,035 | S | 12/2015 | Pal et al. |
| D746,827 | S | 1/2016 | Jung et al. |
| D746,828 | S | 1/2016 | Arai et al. |
| D747,352 | S | 1/2016 | Lee et al. |
| 9,233,204 | B2 | 1/2016 | Booth et al. |
| D749,097 | S | 2/2016 | Zou et al. |
| D749,118 | S | 2/2016 | Wang |
| D751,100 | S | 3/2016 | Lindn et al. |
| D752,604 | S | 3/2016 | Zhang |
| D753,134 | S | 4/2016 | Vazquez |
| D754,718 | S | 4/2016 | Zhou |
| D755,193 | S | 5/2016 | Sun et al. |
| D755,799 | S | 5/2016 | Finnis et al. |
| D755,820 | S | 5/2016 | Wang |
| D756,387 | S | 5/2016 | Chang et al. |
| D757,032 | S | 5/2016 | Sabia et al. |
| D757,035 | S | 5/2016 | Raskin et al. |
| D758,391 | S | 6/2016 | Suarez |
| D758,422 | S | 6/2016 | Zhao |
| D759,032 | S | 6/2016 | Amin et al. |
| D759,078 | S | 6/2016 | Iwamoto |
| D759,678 | S | 6/2016 | Jung et al. |
| D759,687 | S | 6/2016 | Chang et al. |
| D761,812 | S | 7/2016 | Motamedi |
| D763,308 | S | 8/2016 | Wang et al. |
| D763,868 | S | 8/2016 | Lee et al. |
| D765,110 | S | 8/2016 | Liang |
| D765,124 | S | 8/2016 | Minks-Brown et al. |
| 9,402,950 | B2 | 8/2016 | Dilanni et al. |

(56) References Cited

U.S. PATENT DOCUMENTS

| | | |
|---|---|---|
| D765,707 S | 9/2016 | Gomez |
| D766,286 S | 9/2016 | Lee et al. |
| D767,586 S | 9/2016 | Kwon et al. |
| D768,154 S | 10/2016 | Kim et al. |
| D768,188 S | 10/2016 | Li et al. |
| D768,660 S | 10/2016 | Wielgosz |
| D768,685 S | 10/2016 | Lee et al. |
| D769,315 S | 10/2016 | Scotti |
| D770,507 S | 11/2016 | Umezawa et al. |
| D770,515 S | 11/2016 | Cho et al. |
| D771,073 S | 11/2016 | Choi et al. |
| D771,076 S | 11/2016 | Butcher et al. |
| D771,690 S | 11/2016 | Yin et al. |
| D772,911 S | 11/2016 | Lee et al. |
| 9,486,571 B2 | 11/2016 | Rosinko |
| D773,531 S | 12/2016 | Toth et al. |
| D775,184 S | 12/2016 | Song et al. |
| D775,196 S | 12/2016 | Huang et al. |
| 9,520,649 B2 | 12/2016 | De Rochemont |
| D775,658 S | 1/2017 | Luo et al. |
| D776,126 S | 1/2017 | Lai et al. |
| D776,687 S | 1/2017 | Wick et al. |
| D777,191 S | 1/2017 | Polimeni |
| D777,758 S | 1/2017 | Kisselev et al. |
| D781,323 S | 3/2017 | Green et al. |
| D781,781 S | 3/2017 | Schimmoeller, Jr. |
| D781,877 S | 3/2017 | Ko et al. |
| D781,878 S | 3/2017 | Butcher et al. |
| D781,879 S | 3/2017 | Butcher et al. |
| D781,903 S | 3/2017 | Reichle et al. |
| D781,905 S | 3/2017 | Nakaguchi et al. |
| D782,506 S | 3/2017 | Kim et al. |
| D783,672 S | 4/2017 | Rajasankar et al. |
| D785,010 S | 4/2017 | Bachman et al. |
| D785,656 S | 5/2017 | Bramer et al. |
| D786,278 S | 5/2017 | Motamedi |
| D786,898 S | 5/2017 | Hall |
| D788,126 S | 5/2017 | Evnin et al. |
| 9,656,017 B2 | 5/2017 | Greene |
| D788,621 S | 6/2017 | Shallice et al. |
| D788,652 S | 6/2017 | Mutsuro et al. |
| D789,402 S | 6/2017 | Dye et al. |
| D789,967 S | 6/2017 | Kaplan et al. |
| D789,982 S | 6/2017 | Christiana et al. |
| D790,560 S | 6/2017 | Inose et al. |
| D791,781 S | 7/2017 | Donarski et al. |
| D791,805 S | 7/2017 | Segars |
| D791,812 S | 7/2017 | Bistoni et al. |
| D793,412 S | 8/2017 | Chaudhri et al. |
| D795,886 S | 8/2017 | Ng et al. |
| D795,891 S | 8/2017 | Kohan et al. |
| D795,900 S | 8/2017 | Bischoff et al. |
| D795,906 S | 8/2017 | Butrick |
| D795,927 S | 8/2017 | Bischoff et al. |
| 9,743,224 B2 | 8/2017 | San et al. |
| D796,530 S | 9/2017 | Mcmillan et al. |
| D796,540 S | 9/2017 | Mclean et al. |
| D797,116 S | 9/2017 | Chapman et al. |
| D797,763 S | 9/2017 | Kim et al. |
| D797,774 S | 9/2017 | Park et al. |
| D797,797 S | 9/2017 | Gandhi et al. |
| D798,310 S | 9/2017 | Golden et al. |
| D798,311 S | 9/2017 | Golden et al. |
| D799,536 S | 10/2017 | Eder |
| D800,765 S | 10/2017 | Stoksik |
| D800,769 S | 10/2017 | Hennessy et al. |
| D801,383 S | 10/2017 | Park et al. |
| D802,011 S | 11/2017 | Friedman et al. |
| D802,088 S | 11/2017 | Bos et al. |
| D803,232 S | 11/2017 | Leigh et al. |
| D803,242 S | 11/2017 | Mizono et al. |
| D804,502 S | 12/2017 | Amini et al. |
| D805,525 S | 12/2017 | Dascola et al. |
| D806,716 S | 1/2018 | Pahwa et al. |
| D807,376 S | 1/2018 | Mizono et al. |
| D807,400 S | 1/2018 | Lagreca |
| D807,910 S | 1/2018 | Graham et al. |
| D807,918 S | 1/2018 | Cohen et al. |
| D807,919 S | 1/2018 | Cohen et al. |
| D808,423 S | 1/2018 | Jiang et al. |
| D808,974 S | 1/2018 | Chiappone et al. |
| D808,983 S | 1/2018 | Narinedhat et al. |
| 9,857,090 B2 | 1/2018 | Golden et al. |
| D810,116 S | 2/2018 | Mclean et al. |
| D810,771 S | 2/2018 | Gandhi et al. |
| 9,907,515 B2 | 3/2018 | Doyle et al. |
| D815,131 S | 4/2018 | Thompson et al. |
| D816,090 S | 4/2018 | Stonecipher et al. |
| D817,339 S | 5/2018 | Nanjappan et al. |
| D818,491 S | 5/2018 | Timmer et al. |
| D819,057 S | 5/2018 | Huang |
| D819,059 S | 5/2018 | O'Toole |
| 9,980,140 B1 | 5/2018 | Spencer et al. |
| 9,984,773 B2 | 5/2018 | Gondhalekar et al. |
| D820,311 S | 6/2018 | Cabrera et al. |
| D820,862 S | 6/2018 | Alfonzo et al. |
| D822,034 S | 7/2018 | Clymer et al. |
| D822,677 S | 7/2018 | Weaver et al. |
| D822,684 S | 7/2018 | Clausen-Stuck et al. |
| D822,692 S | 7/2018 | Loychik et al. |
| D823,862 S | 7/2018 | Chung et al. |
| D824,400 S | 7/2018 | Chang et al. |
| D824,951 S | 8/2018 | Kolbrener et al. |
| D826,956 S | 8/2018 | Pillalamarri et al. |
| D826,957 S | 8/2018 | Pillalamarri et al. |
| D828,381 S | 9/2018 | Lee et al. |
| D829,732 S | 10/2018 | Jeffrey et al. |
| D830,374 S | 10/2018 | Leonard et al. |
| D830,384 S | 10/2018 | Lepine et al. |
| D830,385 S | 10/2018 | Lepine et al. |
| D830,407 S | 10/2018 | Kisielius et al. |
| D831,033 S | 10/2018 | Leonard et al. |
| D833,469 S | 11/2018 | Coleman et al. |
| D834,601 S | 11/2018 | Felt |
| D835,132 S | 12/2018 | Ito et al. |
| D835,145 S | 12/2018 | Cashner et al. |
| D835,147 S | 12/2018 | Kisielius et al. |
| D835,651 S | 12/2018 | Bao |
| D835,666 S | 12/2018 | Saleh et al. |
| D836,123 S | 12/2018 | Pillalamarri et al. |
| D837,807 S | 1/2019 | Baber et al. |
| D838,731 S | 1/2019 | Pillalamarri et al. |
| D840,418 S | 2/2019 | Saad et al. |
| D840,419 S | 2/2019 | Saad et al. |
| D844,022 S | 3/2019 | Amin |
| D845,317 S | 4/2019 | Wellmeier et al. |
| 10,248,839 B2 | 4/2019 | Levy et al. |
| D848,459 S | 5/2019 | Li |
| D851,099 S | 6/2019 | Uppala et al. |
| D851,658 S | 6/2019 | Pillalamarri et al. |
| 10,335,464 B1 | 7/2019 | Michelich et al. |
| D865,795 S | 11/2019 | Koo |
| D872,746 S | 1/2020 | Laborde |
| D874,471 S | 2/2020 | Pillalamarri et al. |
| D875,114 S | 2/2020 | Clediere |
| 10,583,250 B2 | 3/2020 | Mazlish et al. |
| D880,498 S | 4/2020 | Shahidi et al. |
| D888,070 S | 6/2020 | Yusupov et al. |
| 10,737,024 B2 | 8/2020 | Schmid |
| D904,426 S | 12/2020 | Paul |
| D911,353 S | 2/2021 | Sanchez et al. |
| D914,031 S | 3/2021 | Ding et al. |
| D916,729 S | 4/2021 | Gabriel et al. |
| D916,870 S | 4/2021 | Hemsley |
| D916,878 S | 4/2021 | Kim et al. |
| 10,987,468 B2 | 4/2021 | Mazlish et al. |
| D918,261 S | 5/2021 | Ramamurthy et al. |
| D920,351 S | 5/2021 | Zhang |
| D923,033 S | 6/2021 | Smith et al. |
| D927,533 S | 8/2021 | Clymer |
| D938,447 S | 12/2021 | Holland |
| 11,197,964 B2 | 12/2021 | Sjolund et al. |
| 11,260,169 B2 | 3/2022 | Estes |
| D954,078 S | 6/2022 | Rahate et al. |

(56) References Cited

U.S. PATENT DOCUMENTS

| | | |
|---|---|---|
| 2001/0034023 A1 | 10/2001 | Stanton et al. |
| 2001/0034502 A1 | 10/2001 | Moberg et al. |
| 2001/0048969 A1 | 12/2001 | Constantino et al. |
| 2001/0051377 A1 | 12/2001 | Hammer et al. |
| 2001/0056258 A1 | 12/2001 | Evans |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0047768 A1 | 4/2002 | Duffy |
| 2002/0070983 A1 | 6/2002 | Kozub et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2002/0173769 A1 | 11/2002 | Gray et al. |
| 2002/0190818 A1 | 12/2002 | Endou et al. |
| 2003/0023148 A1 | 1/2003 | Lorenz et al. |
| 2003/0034124 A1 | 2/2003 | Sugaya et al. |
| 2003/0040715 A1 | 2/2003 | D'Antonio et al. |
| 2003/0050621 A1 | 3/2003 | Lebel et al. |
| 2003/0060692 A1 | 3/2003 | Ruchti et al. |
| 2003/0086073 A1 | 5/2003 | Braig et al. |
| 2003/0100040 A1 | 5/2003 | Bonnecaze et al. |
| 2003/0122647 A1 | 7/2003 | Ou |
| 2003/0135388 A1 | 7/2003 | Martucci et al. |
| 2003/0144582 A1 | 7/2003 | Cohen et al. |
| 2003/0148024 A1 | 8/2003 | Kodas et al. |
| 2003/0163097 A1 | 8/2003 | Fleury et al. |
| 2003/0163223 A1 | 8/2003 | Blomquist |
| 2003/0170436 A1 | 9/2003 | Sumi et al. |
| 2003/0175806 A1 | 9/2003 | Rule et al. |
| 2003/0195404 A1 | 10/2003 | Knobbe et al. |
| 2003/0208113 A1 | 11/2003 | Mault et al. |
| 2003/0212379 A1 | 11/2003 | Bylund et al. |
| 2003/0216627 A1 | 11/2003 | Lorenz et al. |
| 2003/0220605 A1 | 11/2003 | Bowman et al. |
| 2003/0221621 A1 | 12/2003 | Pokharna et al. |
| 2004/0010207 A1 | 1/2004 | Flaherty et al. |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0068224 A1 | 4/2004 | Couvillon et al. |
| 2004/0069004 A1 | 4/2004 | Gist et al. |
| 2004/0069044 A1 | 4/2004 | Lavi et al. |
| 2004/0087904 A1 | 5/2004 | Langley et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1* | 11/2004 | Starkweather ......... G16H 20/17 |
| | | 128/923 |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0038680 A1 | 2/2005 | McMahon |
| 2005/0043598 A1 | 2/2005 | Goode et al. |
| 2005/0049179 A1 | 3/2005 | Davidson et al. |
| 2005/0065464 A1 | 3/2005 | Talbot et al. |
| 2005/0075624 A1 | 4/2005 | Miesel |
| 2005/0105095 A1 | 5/2005 | Pesach et al. |
| 2005/0134609 A1 | 6/2005 | Yu |
| 2005/0137573 A1 | 6/2005 | McLaughlin |
| 2005/0182306 A1 | 8/2005 | Sloan |
| 2005/0182366 A1 | 8/2005 | Vogt et al. |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0238507 A1 | 10/2005 | Diianni et al. |
| 2005/0261660 A1 | 11/2005 | Choi |
| 2005/0262451 A1 | 11/2005 | Remignanti et al. |
| 2005/0272640 A1 | 12/2005 | Doyle et al. |
| 2005/0277912 A1 | 12/2005 | John |
| 2006/0009727 A1 | 1/2006 | O'Mahony et al. |
| 2006/0041229 A1 | 2/2006 | Garibotto et al. |
| 2006/0064053 A1 | 3/2006 | Bollish et al. |
| 2006/0079765 A1 | 4/2006 | Neer et al. |
| 2006/0086994 A1 | 4/2006 | Mefers et al. |
| 2006/0134323 A1 | 6/2006 | O'Brien |
| 2006/0134491 A1 | 6/2006 | Hilchenko et al. |
| 2006/0167350 A1 | 7/2006 | Monfre et al. |
| 2006/0178633 A1 | 8/2006 | Garibotto et al. |
| 2006/0189925 A1 | 8/2006 | Gable et al. |
| 2006/0189926 A1 | 8/2006 | Hall et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253067 A1 | 11/2006 | Staib et al. |
| 2006/0253085 A1 | 11/2006 | Geismar et al. |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0100222 A1 | 5/2007 | Mastrototaro et al. |
| 2007/0100635 A1 | 5/2007 | Mahajan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0166453 A1 | 7/2007 | Van et al. |
| 2007/0168145 A1 | 7/2007 | Beyer et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0259768 A1 | 11/2007 | Kear et al. |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0033320 A1 | 2/2008 | Racchini et al. |
| 2008/0051738 A1 | 2/2008 | Griffin |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0114304 A1 | 5/2008 | Nalesso et al. |
| 2008/0132880 A1 | 6/2008 | Buchman |
| 2008/0160492 A1 | 7/2008 | Campbell et al. |
| 2008/0172026 A1 | 7/2008 | Blomquist |
| 2008/0172028 A1 | 7/2008 | Blomquist |
| 2008/0188796 A1 | 8/2008 | Steil et al. |
| 2008/0200838 A1 | 8/2008 | Goldberger et al. |
| 2008/0201325 A1 | 8/2008 | Doniger et al. |
| 2008/0206067 A1 | 8/2008 | De et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0234663 A1 | 9/2008 | Yodfat et al. |
| 2008/0249386 A1 | 10/2008 | Besterman et al. |
| 2008/0250341 A1 | 10/2008 | Dlugos et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |

(56) References Cited

U.S. PATENT DOCUMENTS

| | | |
|---|---|---|
| 2008/0306353 A1 | 12/2008 | Douglas et al. |
| 2008/0319384 A1 | 12/2008 | Yodfat et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0112154 A1 | 4/2009 | Montgomery et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0164251 A1 | 6/2009 | Hayter |
| 2009/0198350 A1 | 8/2009 | Thiele |
| 2009/0204341 A1 | 8/2009 | Brauker et al. |
| 2009/0212966 A1 | 8/2009 | Panduro |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2009/0326472 A1 | 12/2009 | Carter et al. |
| 2010/0017141 A1 | 1/2010 | Campbell et al. |
| 2010/0036326 A1 | 2/2010 | Matusch |
| 2010/0049022 A1 | 2/2010 | Parris et al. |
| 2010/0057042 A1 | 3/2010 | Hayter |
| 2010/0064243 A1 | 3/2010 | Buck et al. |
| 2010/0075353 A1 | 3/2010 | Heaton |
| 2010/0077198 A1 | 3/2010 | Buck et al. |
| 2010/0082167 A1 | 4/2010 | Haueter et al. |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0137788 A1 | 6/2010 | Braithwaite et al. |
| 2010/0138097 A1 | 6/2010 | Ku et al. |
| 2010/0145262 A1 | 6/2010 | Bengtsson et al. |
| 2010/0145272 A1 | 6/2010 | Cefai et al. |
| 2010/0152658 A1 | 6/2010 | Hanson et al. |
| 2010/0174228 A1 | 7/2010 | Buckingham et al. |
| 2010/0174266 A1 | 7/2010 | Estes |
| 2010/0185183 A1 | 7/2010 | Alme et al. |
| 2010/0211003 A1 | 8/2010 | Sundar et al. |
| 2010/0228110 A1 | 9/2010 | Tsoukalis |
| 2010/0241066 A1 | 9/2010 | Hansen et al. |
| 2010/0249561 A1 | 9/2010 | Patek et al. |
| 2010/0256466 A1 | 10/2010 | Shekalim et al. |
| 2010/0262117 A1 | 10/2010 | Magni et al. |
| 2010/0262434 A1 | 10/2010 | Shaya |
| 2010/0292634 A1 | 11/2010 | Kircher et al. |
| 2010/0295686 A1 | 11/2010 | Sloan et al. |
| 2010/0317952 A1 | 12/2010 | Budiman et al. |
| 2011/0009725 A1 | 1/2011 | Hill et al. |
| 2011/0009813 A1 | 1/2011 | Rankers |
| 2011/0021584 A1 | 1/2011 | Berggren et al. |
| 2011/0021898 A1 | 1/2011 | Wei et al. |
| 2011/0028817 A1 | 2/2011 | Jin et al. |
| 2011/0029034 A1 | 2/2011 | Fischer et al. |
| 2011/0049394 A1 | 3/2011 | De Rochemont |
| 2011/0054390 A1 | 3/2011 | Searle et al. |
| 2011/0054399 A1 | 3/2011 | Chong et al. |
| 2011/0065224 A1 | 3/2011 | Bollman et al. |
| 2011/0071765 A1 | 3/2011 | Yodfat et al. |
| 2011/0077493 A1 | 3/2011 | Shadforth et al. |
| 2011/0098548 A1 | 4/2011 | Budiman et al. |
| 2011/0098674 A1* | 4/2011 | Vicente ............ G06F 1/1684 |
| | | 713/503 |
| 2011/0106011 A1 | 5/2011 | Cinar et al. |
| 2011/0106050 A1 | 5/2011 | Yodfat et al. |
| 2011/0118987 A1 | 5/2011 | Takeuchi et al. |
| 2011/0124996 A1 | 5/2011 | Reinke et al. |
| 2011/0144586 A1 | 6/2011 | Michaud et al. |
| 2011/0160555 A1 | 6/2011 | Reifman et al. |
| 2011/0160652 A1 | 6/2011 | Yodfat et al. |
| 2011/0178472 A1 | 7/2011 | Cabiri |
| 2011/0184267 A1 | 7/2011 | Duke et al. |
| 2011/0190694 A1 | 8/2011 | Lanier et al. |
| 2011/0202005 A1 | 8/2011 | Yodfat et al. |
| 2011/0208156 A1 | 8/2011 | Doyle et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0264071 A1 | 10/2011 | Braig et al. |
| 2011/0266999 A1 | 11/2011 | Yodfat et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010592 A1 | 1/2012 | Brown |
| 2012/0030393 A1 | 2/2012 | Ganesh et al. |
| 2012/0053556 A1 | 3/2012 | Lee |
| 2012/0059351 A1 | 3/2012 | Nordh |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0124521 A1 | 5/2012 | Guo |
| 2012/0136336 A1 | 5/2012 | Mastrototaro et al. |
| 2012/0150446 A1 | 6/2012 | Chang et al. |
| 2012/0165638 A1 | 6/2012 | Duke et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0246106 A1 | 9/2012 | Atlas et al. |
| 2012/0250449 A1 | 10/2012 | Nakano |
| 2012/0271655 A1 | 10/2012 | Knobel et al. |
| 2012/0277667 A1 | 11/2012 | Yodat et al. |
| 2012/0277668 A1 | 11/2012 | Chawla |
| 2012/0282111 A1 | 11/2012 | Nip et al. |
| 2012/0283694 A1 | 11/2012 | Yodfat et al. |
| 2012/0295550 A1 | 11/2012 | Wilson et al. |
| 2012/0330227 A1 | 12/2012 | Budiman et al. |
| 2013/0030358 A1 | 1/2013 | Yodfat et al. |
| 2013/0046281 A1 | 2/2013 | Javitt |
| 2013/0072872 A1 | 3/2013 | Yodfat et al. |
| 2013/0079613 A1 | 3/2013 | Kovatchev et al. |
| 2013/0158503 A1 | 6/2013 | Kanderian et al. |
| 2013/0172695 A1 | 7/2013 | Nielsen et al. |
| 2013/0172710 A1 | 7/2013 | Mears et al. |
| 2013/0178791 A1 | 7/2013 | Javitt |
| 2013/0231642 A1 | 9/2013 | Doyle et al. |
| 2013/0245545 A1 | 9/2013 | Arnold et al. |
| 2013/0245547 A1 | 9/2013 | El-Khatib et al. |
| 2013/0253472 A1 | 9/2013 | Cabiri |
| 2013/0261406 A1 | 10/2013 | Rebec et al. |
| 2013/0296792 A1 | 11/2013 | Cabiri |
| 2013/0296823 A1 | 11/2013 | Melker et al. |
| 2013/0298080 A1 | 11/2013 | Griffin et al. |
| 2013/0317753 A1 | 11/2013 | Kamen et al. |
| 2013/0332874 A1 | 12/2013 | Rosinko et al. |
| 2013/0338576 A1 | 12/2013 | O'Connor et al. |
| 2013/0346858 A1 | 12/2013 | Neyrinck |
| 2014/0005633 A1 | 1/2014 | Finan |
| 2014/0018730 A1 | 1/2014 | Stephan |
| 2014/0032549 A1 | 1/2014 | Mcdaniel et al. |
| 2014/0066859 A1 | 3/2014 | Ogawa et al. |
| 2014/0066886 A1 | 3/2014 | Roy et al. |
| 2014/0066887 A1 | 3/2014 | Mastrototaro et al. |
| 2014/0074033 A1 | 3/2014 | Sonderegger et al. |
| 2014/0088428 A1 | 3/2014 | Yang et al. |
| 2014/0108046 A1 | 4/2014 | Echeverria et al. |
| 2014/0121635 A1 | 5/2014 | Hayter |
| 2014/0128705 A1 | 5/2014 | Mazlish |
| 2014/0128839 A1 | 5/2014 | Diianni et al. |
| 2014/0129951 A1 | 5/2014 | Amin et al. |
| 2014/0135880 A1 | 5/2014 | Baumgartner et al. |

(56)        References Cited

U.S. PATENT DOCUMENTS

| | | |
|---|---|---|
| 2014/0142508 A1 | 5/2014 | Diianni et al. |
| 2014/0146202 A1 | 5/2014 | Boss et al. |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2014/0350369 A1 | 11/2014 | Budiman et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0025503 A1 | 1/2015 | Searle et al. |
| 2015/0041498 A1 | 2/2015 | Kakiuchi et al. |
| 2015/0120317 A1 | 4/2015 | Mayou et al. |
| 2015/0134265 A1 | 5/2015 | Kohlbrecher et al. |
| 2015/0134353 A1 | 5/2015 | Ferrell et al. |
| 2015/0165117 A1 | 6/2015 | Palerm et al. |
| 2015/0165119 A1 | 6/2015 | Palerm et al. |
| 2015/0173674 A1 | 6/2015 | Hayes et al. |
| 2015/0193585 A1 | 7/2015 | Sunna |
| 2015/0202386 A1 | 7/2015 | Brady et al. |
| 2015/0205509 A1 | 7/2015 | Scriven et al. |
| 2015/0205511 A1 | 7/2015 | Mnna et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0289823 A1 | 10/2015 | Rack-Gomer et al. |
| 2015/0301691 A1 | 10/2015 | Qin |
| 2015/0306314 A1 | 10/2015 | Doyle et al. |
| 2015/0331995 A1 | 11/2015 | Zhao et al. |
| 2015/0351671 A1 | 12/2015 | Vanslyke et al. |
| 2015/0351672 A1 | 12/2015 | Vanslyke et al. |
| 2015/0356250 A1 | 12/2015 | Polimeni |
| 2016/0015891 A1 | 1/2016 | Papiorek |
| 2016/0019352 A1 | 1/2016 | Cohen et al. |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0220181 A1 | 8/2016 | Rigoard et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0007882 A1 | 1/2017 | Werner |
| 2017/0021096 A1 | 1/2017 | Cole et al. |
| 2017/0049386 A1 | 2/2017 | Abraham et al. |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0173261 A1 | 6/2017 | O'Connor et al. |
| 2017/0182248 A1 | 6/2017 | Rosinko |
| 2017/0188943 A1 | 7/2017 | Braig et al. |
| 2017/0189625 A1 | 7/2017 | Cirillo et al. |
| 2017/0216524 A1 | 8/2017 | Haider et al. |
| 2017/0239415 A1 | 8/2017 | Hwang et al. |
| 2017/0258987 A1 | 9/2017 | Caspers |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0347971 A1 | 12/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Afonso |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0095052 A1 | 3/2019 | De et al. |
| 2019/0132801 A1 | 5/2019 | Kamath et al. |
| 2019/0184091 A1 | 6/2019 | Sjolund et al. |
| 2019/0240403 A1 | 8/2019 | Palerm et al. |
| 2019/0290844 A1 | 9/2019 | Monirabbasi et al. |
| 2019/0321545 A1 | 10/2019 | Saint |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2019/0374714 A1 | 12/2019 | Rioux et al. |
| 2020/0001006 A1 | 1/2020 | Pizzochero et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0113515 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |
| 2022/0105270 A1 | 4/2022 | Doyle et al. |

FOREIGN PATENT DOCUMENTS

| | | |
|---|---|---|
| CA | 3026851 A1 | 2/2020 |
| CN | 1297140 A | 5/2001 |
| DE | 4200595 A1 | 7/1993 |
| DE | 19756872 A1 | 7/1999 |
| EP | 0549341 A1 | 6/1993 |
| EP | 1177802 B1 | 9/2004 |
| EP | 1571582 A2 | 9/2005 |
| EP | 2397181 A1 | 12/2011 |
| EP | 2468338 A1 | 6/2012 |
| EP | 2897071 A1 | 7/2015 |
| FR | 2096275 A5 | 2/1972 |
| JP | 02-131777 A | 5/1990 |
| JP | 2004-283378 A | 10/2004 |
| JP | 2005-326943 A | 11/2005 |
| JP | 2008-545454 A | 12/2008 |
| JP | 2010-531678 A | 9/2010 |
| JP | 2018-153569 A | 10/2018 |
| TW | M452390 U | 5/2013 |
| WO | 86/06796 A1 | 11/1986 |
| WO | 98/00193 A1 | 1/1998 |
| WO | 98/55073 A1 | 12/1998 |
| WO | 99/10040 A1 | 3/1999 |
| WO | 99/10049 A1 | 3/1999 |
| WO | 99/56803 A1 | 11/1999 |
| WO | 99/62576 A1 | 12/1999 |
| WO | 00/30705 A1 | 6/2000 |
| WO | 00/32258 A1 | 6/2000 |
| WO | 00/48112 A2 | 8/2000 |
| WO | 01/72354 A2 | 10/2001 |
| WO | 01/78812 A1 | 10/2001 |
| WO | 02/15954 A1 | 2/2002 |
| WO | 02/26282 A2 | 4/2002 |
| WO | 02/43866 A2 | 6/2002 |
| WO | 03/16882 A1 | 2/2003 |
| WO | 03/97133 A1 | 11/2003 |

(56)  References Cited

FOREIGN PATENT DOCUMENTS

| | | | |
|---|---|---|---|
| WO | 2004/043250 | A1 | 5/2004 |
| WO | 2004/092715 | A1 | 10/2004 |
| WO | 2005/051170 | A2 | 6/2005 |
| WO | 2005/082436 | A1 | 9/2005 |
| WO | 2005/110601 | A1 | 11/2005 |
| WO | 2005/113036 | A1 | 12/2005 |
| WO | 2006/053007 | A2 | 5/2006 |
| WO | 2006/124716 | A3 | 3/2007 |
| WO | 2007/064835 | A2 | 6/2007 |
| WO | 2007/066152 | A2 | 6/2007 |
| WO | 2007/078937 | A2 | 7/2007 |
| WO | 2008/024810 | A2 | 2/2008 |
| WO | 2008/029403 | A1 | 3/2008 |
| WO | 2008/057384 | A3 | 9/2008 |
| WO | 2008/133702 | A1 | 11/2008 |
| WO | 2008/157780 | A1 | 12/2008 |
| WO | 2009/039203 | A2 | 3/2009 |
| WO | 2009/045462 | A1 | 4/2009 |
| WO | 2009/049252 | A1 | 4/2009 |
| WO | 2009/066287 | A2 | 5/2009 |
| WO | 2009/066288 | A1 | 5/2009 |
| WO | 2009/098648 | A2 | 8/2009 |
| WO | 2009/134380 | A2 | 11/2009 |
| WO | 2010/022069 | A2 | 2/2010 |
| WO | 2010/053702 | A1 | 5/2010 |
| WO | 2010/077279 | A1 | 7/2010 |
| WO | 2010/132077 | A1 | 11/2010 |
| WO | 2010/138848 | A1 | 12/2010 |
| WO | 2010/139793 | A1 | 12/2010 |
| WO | 2010/147659 | A2 | 12/2010 |
| WO | 2011/031458 | A1 | 3/2011 |
| WO | 2011/075042 | A1 | 6/2011 |
| WO | 2011/095483 | A1 | 8/2011 |
| WO | 2011/133823 | A1 | 10/2011 |
| WO | 2012/045667 | A2 | 4/2012 |
| WO | 2012/073032 | A1 | 6/2012 |
| WO | 2012/108959 | A1 | 8/2012 |
| WO | 2012/134588 | A1 | 10/2012 |
| WO | 2012/177353 | A1 | 12/2012 |
| WO | 2012/178134 | A2 | 12/2012 |
| WO | 2013/050535 | A2 | 4/2013 |
| WO | 2013/066849 | A1 | 5/2013 |
| WO | 2013/078200 | A1 | 5/2013 |
| WO | 2013/096769 | A1 | 6/2013 |
| WO | 2013/134486 | A2 | 9/2013 |
| WO | 2013/149186 | A1 | 10/2013 |
| WO | 2013/177565 | A1 | 11/2013 |
| WO | 2013/182321 | A1 | 12/2013 |
| WO | 2014/029416 | A1 | 2/2014 |
| WO | 2014/035570 | A2 | 3/2014 |
| WO | 2014/109898 | A1 | 7/2014 |
| WO | 2014/110538 | A1 | 7/2014 |
| WO | 2014/149357 | A1 | 9/2014 |
| WO | 2014/179774 | A1 | 11/2014 |
| WO | 2014/194183 | A2 | 12/2014 |
| WO | 2015/056259 | A1 | 4/2015 |
| WO | 2015/061493 | A1 | 4/2015 |
| WO | 2015/073211 | A1 | 5/2015 |
| WO | 2015/081337 | A2 | 6/2015 |
| WO | 2015/117082 | A1 | 8/2015 |
| WO | 2015/117854 | A1 | 8/2015 |
| WO | 2015/167201 | A1 | 11/2015 |
| WO | 2015/177082 | A1 | 11/2015 |
| WO | 2015/187366 | A1 | 12/2015 |
| WO | 2016/004088 | A1 | 1/2016 |
| WO | 2016/022650 | A1 | 2/2016 |
| WO | 2016/041873 | A1 | 3/2016 |
| WO | 2016/089702 | A1 | 6/2016 |
| WO | 2016/141082 | A1 | 9/2016 |
| WO | 2016/161254 | A1 | 10/2016 |
| WO | 2017/004278 | A1 | 1/2017 |
| WO | 2017/027459 | A1 | 2/2017 |
| WO | 2017/091624 | A1 | 6/2017 |
| WO | 2017/105600 | A1 | 6/2017 |
| WO | 2017/184988 | A1 | 10/2017 |
| WO | 2017/187177 | A1 | 11/2017 |
| WO | 2017/205816 | A1 | 11/2017 |
| WO | 2018/009614 | A1 | 1/2018 |
| WO | 2018/067748 | A1 | 4/2018 |
| WO | 2018/120104 | A1 | 7/2018 |
| WO | 2018/136799 | A1 | 7/2018 |
| WO | 2018/204568 | A1 | 11/2018 |
| WO | 2019/077482 | A1 | 4/2019 |
| WO | 2019/094440 | A1 | 5/2019 |
| WO | 2019/213493 | A1 | 11/2019 |
| WO | 2019/246381 | A1 | 12/2019 |
| WO | 2020/081393 | A1 | 4/2020 |
| WO | 2021/011738 | A1 | 1/2021 |

OTHER PUBLICATIONS

European Examination Report for European Application No. 14726270.3 dated Mar. 23, 2018, six pages.

Annex to the communication Mailed on Mar. 23, 2018 for EP Application No. 14726270.

Cameron, Fraser, et al. "Statistical hypoglycemia prediction." &nbssp;Journal of diabetes science and technology 2.4 (2008): 612-621. (Year: 2008).

International Search Report for PCT Application No. PCT/US2014/034383 dated Jul. 30, 2014, four pages.

Leon-Vargas, F. et al; "Postprandial blood glucose control using a hybrid adaptive PD controller with insulin-on-board limitation"; Biomedical Signal Processing and Control 8 (2013) 724-732.

Mazlish; U.S. Pat. App. entitled "Insulin delivery systems and methods," filed Jun. 8, 2015, U.S. Appl. No. 14/733,567.

Mudaliar et al.; Insulin aspart (B28 Asp-insulin): A fast-acting analog of human insulin; Diabetes Care; 22(9); pp. 1501-1506; Sep. 1999.

Pennant et al.; Insulin administration and rate of glucose appearance in people with type 1 diabetes; Diabetes Care; 31(11); pp. 2183-2187; Nov. 2008.

Search Report received in International Application No. PCT/US17/34012, Aug. 17, 2017.

Swan et al.; Effect of age of infusion site and type of rapid-acting analog on pharmacodynamic parameters of insulin boluses in youth with type 1 diabetes receiving insulin pump therapy; Diabetes Care; 32(2); pp. 240-244; Feb. 2009.

Written Opinion of the International Searching Authority for PCT Application No. PCT/US2014/034383 dated Jul. 30, 2014, nine pages.

Written Opinion of the International Searching Authority, as issued in connection with the International Patent Application No. PCT/US17/34012 dated Aug. 17, 2017.

Hovorka, Roman, et al. "Nonlinear model predictive control of glucose concentration in subjects with type 1 diabetes." Physiological measurement 25.4 (2004): 905. (Year: 2004).

Anonymous, Insulin pump, Wikipedia, May 23, 2014 revision, URL: https://en.wikipedia.org/w/index.php?title=Insulin_pump&oldid=609808946, retrieved on Sep. 23, 2023, 11 pages.

European Communication pursuant to Article 94(3) EPC for European Application No. 23169309.4, dated Oct. 31, 2023, 10 pages.

European Search Report for European Application No. 23169309.4, dated Oct. 2, 2023, 5 pages.

Communication pursuant to Article 94(3) EPC of European Patent Application No. 23 169 309.4, mailed Mar. 23, 2026, 11 pages.

* cited by examiner

DISCRETIONARY INSULIN DELIVERY SYSTEMS AND METHODS

CROSS REFERENCE TO RELATED APPLICATIONS

This application is a continuation of U.S. patent application Ser. No. 14/254,684, filed Apr. 16, 2014 and entitled "Discretionary Insulin Delivery Systems and Methods," which claims the benefit of the priority dates under 35 U.S.C. 119 of U.S. Provisional Application No. 61/812,452 filed Apr. 16, 2013 and entitled "Discretionary Insulin Delivery Systems and Methods," and of U.S. Provisional Application No. 61/908,981 filed Nov. 26, 2013 and entitled "Discretionary Insulin Delivery," the contents and disclosure of each of which is hereby incorporated herein in its entirety by this reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates to the discretionary delivery of insulin to a user (e.g., a person with diabetes) and, more particularly, this disclosure relates to systems and methods for delivering a discretionary dose of insulin to a user.

BACKGROUND

Diabetes mellitus is a chronic metabolic disorder caused by an inability of a person's pancreas to produce sufficient amounts of insulin, such that the person's metabolism is unable to provide for the proper absorption of sugar and starch. This failure leads to hyperglycemia, i.e., the presence of an excessive amount of analyte within the blood plasma. Persistent hyperglycemia has been associated with a variety of serious symptoms and life-threatening long-term complications such as dehydration, ketoacidosis, diabetic coma, cardiovascular diseases, chronic renal failure, retinal damage and nerve damages with the risk of amputation of extremities. Because healing is not yet possible, a permanent therapy is necessary that provides constant glycemic control in order to constantly maintain the level of blood analyte within normal limits. Such glycemic control is achieved by regularly supplying external drugs to the body of the patient to thereby reduce the elevated levels of blood analyte.

An external biologically effective drug (e.g., insulin or its analog) was commonly administered by means of multiple, daily injections of a mixture of rapid and intermediate acting drug via a hypodermic syringe. While this treatment does not require the frequent estimation of blood analyte, it has been found that the degree of glycemic control achievable in this way is suboptimal because the delivery is unlike physiological drug production, according to which drug(s) enters the bloodstream at a lower rate and over a more extended period of time.

Improved glycemic control may be achieved by the so-called intensive drug therapy which is based on multiple daily injections, including one or two injections per day of a long acting drug for providing basal drug and additional injections of a rapidly acting drug before each meal in an amount proportional to the size of the meal. Although traditional syringes have at least partly been replaced by drug pens, the frequent injections are nevertheless very inconvenient for the patient, particularly those who are incapable of reliably self-administering injections.

Substantial improvements in diabetes therapy have been achieved by the development of other drug delivery devices, such as insulin pumps, relieving the patient of the need for syringes or drug pens and the administration of multiple, daily injections. Insulin pumps allow for the delivery of insulin in a manner that bears greater similarity to the naturally occurring physiological processes and can be controlled to follow standard or individually modified protocols to give the patient better glycemic control.

In addition, delivery directly into the intraperitoneal space or intravenously can be achieved by drug delivery devices. Drug delivery devices can be constructed as an implantable device for subcutaneous arrangement or can be constructed as an external device with an infusion set for subcutaneous infusion to the patient via the transcutaneous insertion of a catheter, cannula or a transdermal drug transport such as through a patch. External drug delivery devices are mounted on clothing, hidden beneath or inside clothing, or mounted on the body and are generally controlled via a user interface built-in to the device or on a separate remote device.

Drug delivery devices have been utilized to assist in the management of diabetes by infusing drug or a suitable biologically effective material into the diabetic patient at a basal rate with additional drug or "bolus" to account for meals or high analyte values, levels or concentrations. The drug delivery device typically is connected to an infuser, better known as an infusion set, by a flexible hose. The infuser typically has a subcutaneous cannula, and an adhesive backed mount on which the cannula is attached. The cannula may include a quick disconnect to allow the cannula and mount to remain in place on the skin surface of the user while the flexible tubing is disconnected from the infuser. Regardless of the type of drug delivery device, blood analyte monitoring is typically required to achieve acceptable glycemic control. For example, delivery of suitable amounts of drug by the drug delivery device requires that the patient frequently determine his or her blood analyte level and manually input this value into a user interface for the external drug delivery device, which then may calculate a suitable modification to the default or currently in-use drug delivery protocol, i.e., dosage and timing, and subsequently communicates with the drug delivery device to adjust its operation accordingly. The determination of blood analyte concentration is typically performed by means of an episodic measuring device such as a hand-held electronic meter which receives blood samples via enzyme-based test strips and calculates the blood analyte value based on the enzymatic reaction. In recent years, continuous analyte monitoring has also been utilized with drug delivery devices to allow for greater control of the drug(s) being infused into the diabetic patients.

People with diabetes should maintain tight control over their lifestyle, so that they are not adversely affected by, for example, irregular food consumption, exercise or stress. In addition, a physician dealing with a particular individual with diabetes may require detailed information on the individual's lifestyle to provide effective treatment or modification of treatment for controlling diabetes. Currently, one of the ways of monitoring the lifestyle of an individual with diabetes has been for the individual to keep a paper logbook of their lifestyle. Another way is for an individual to simply rely on remembering facts about their lifestyle and then relay these details to their physician on each visit.

The aforementioned methods of recording lifestyle information are inherently difficult, time consuming, and often inaccurate. Paper logbooks are not necessarily always carried by an individual and may not be accurately completed when required. Such paper logbooks are small and it is therefore difficult to enter detailed information requiring detailed descriptors of lifestyle events. Furthermore, an individual may often forget key facts about their lifestyle when questioned by a physician who has to manually review and interpret information from a hand-written notebook. There is no analysis provided by the paper logbook to distill or separate the component information. Also, there are no graphical reductions or summary of the information. Entry of data into a secondary data storage system, such as a database or other electronic system, requires a laborious transcription of information, including lifestyle data, into this secondary data storage. Difficulty of data recordation encourages retrospective entry of pertinent information that results in inaccurate and incomplete records.

In light of the many deficiencies and problems associated with current systems and methods for maintaining proper glycemic control, enormous resources have been put into finding better solutions. It has been contemplated for many years that it should be entirely feasible to couple a continuous glucose monitoring system with an insulin delivery device to provide an "artificial pancreas" to assist people living with diabetes. However, developing such workable solutions to the problem that are simple, safe, reliable and able to gain regulatory approval has proved to be elusive. What has been needed and has not been provided by the prior art is a system and method that provide a level of automatic control of insulin delivery devices for improved insulin delivery and glycemic control that is simple, safe, and reliable in a real world setting.

BRIEF SUMMARY

In one aspect, a method of facilitating delivery of a discretionary dose of insulin to a user includes: enabling the person to specify parameters associated with a discretionary delivery of insulin that may be delivered to the user; subsequently receiving data that represents the user's glucose level during a period of time associated with the discretionary delivery; automatically determining, based on the received data, if, when and how much discretionary insulin should be delivered to the user during the period of time associated with the discretionary delivery; and delivering insulin to the user during the period of time associated with the discretionary delivery according to the automatic determination.

Also disclosed is a computer-based system configured to perform various implementations of the foregoing method.

In general, the period of time associated with the discretionary delivery can be any period of time, during which the computer-based system is authorized to deliver one or more doses of insulin to the user at the system's discretion. This period of time may be something that the user or a caregiver has specified in setting up the parameters for the discretionary delivery. However, the period of time need not be particularly specified by the user or caregiver. The period of time may be a single discrete time period. Alternatively, it may be one of a series of consecutive or non-consecutive time periods. Finally, the period of time can be of virtually any duration.

The discretionary insulin delivery can be in addition to insulin delivered pursuant to a non-discretionary insulin delivery schedule or in lieu of some or all of the insulin that would have been delivered pursuant to a non-discretionary insulin delivery schedule.

In some implementations, the method includes delivering insulin, with an insulin delivery pump, to the user according to a non-discretionary insulin delivery schedule unless the computer-based processor determines that a discretionary insulin delivery should occur. According to some implementations, the method includes, receiving data at the computer-based processor that represents an amount and timing of insulin that has been or will be delivered to the user by the insulin delivery pump over time. In those implementations, automatically determining if, when and how much discretionary insulin should be delivered to the user during the period of time associated with the discretionary delivery can be based, at least in part, on the data that represents an amount and timing of insulin that has been or will be delivered to the user over time.

In certain implementations, delivery of a discretionary dose of insulin may be constrained, even if the user's recent glucose readings show an upward trend, for example. In some implementations, the delivery of discretionary insulin to the user constraint may be based on estimated insulin-on-board for the user. In other implementations, discretionary delivery may be constrained if a recent glucose reading is below or above a certain threshold.

Some implementations include an alarm. For example, in some implementations, the method includes triggering the alarm if the delivery of discretionary insulin has been terminated because a cumulative amount of discretionary insulin delivered during a specific time period exceeded a threshold amount. Moreover, typically, the user can acknowledge the alarm. If the alarm is acknowledged within a predetermined amount of time after the alarm is triggered, the method includes subsequently delivering insulin to the user according to a non-discretionary insulin delivery schedule. If the alarm is not acknowledged within the predetermined amount of time after the alarm is triggered, the method includes subsequently delivering less insulin than would be delivered according to the non-discretionary insulin delivery schedule.

In some implementations, one or more of the following advantages may be present.

For example, insulin can be delivered to people who need it in closer correspondence to exactly how much insulin they need and when they need it. Mis-estimation of insulin requirements is a common problem for users with diabetes and allowing the automatic determination to either reduce or increase the insulin delivery automatically has the potential to significantly mitigate some of the burdens of managing diabetes. Moreover, the discretion that a system can automatically exercise in augmented delivery of insulin is made highly safe by virtue of the alarming and automatic correction of a possible over-delivery functionality disclosed herein.

Other features and advantages will be apparent from other portions of this specification, including the drawings.

DETAILED DESCRIPTION

Figure 1:
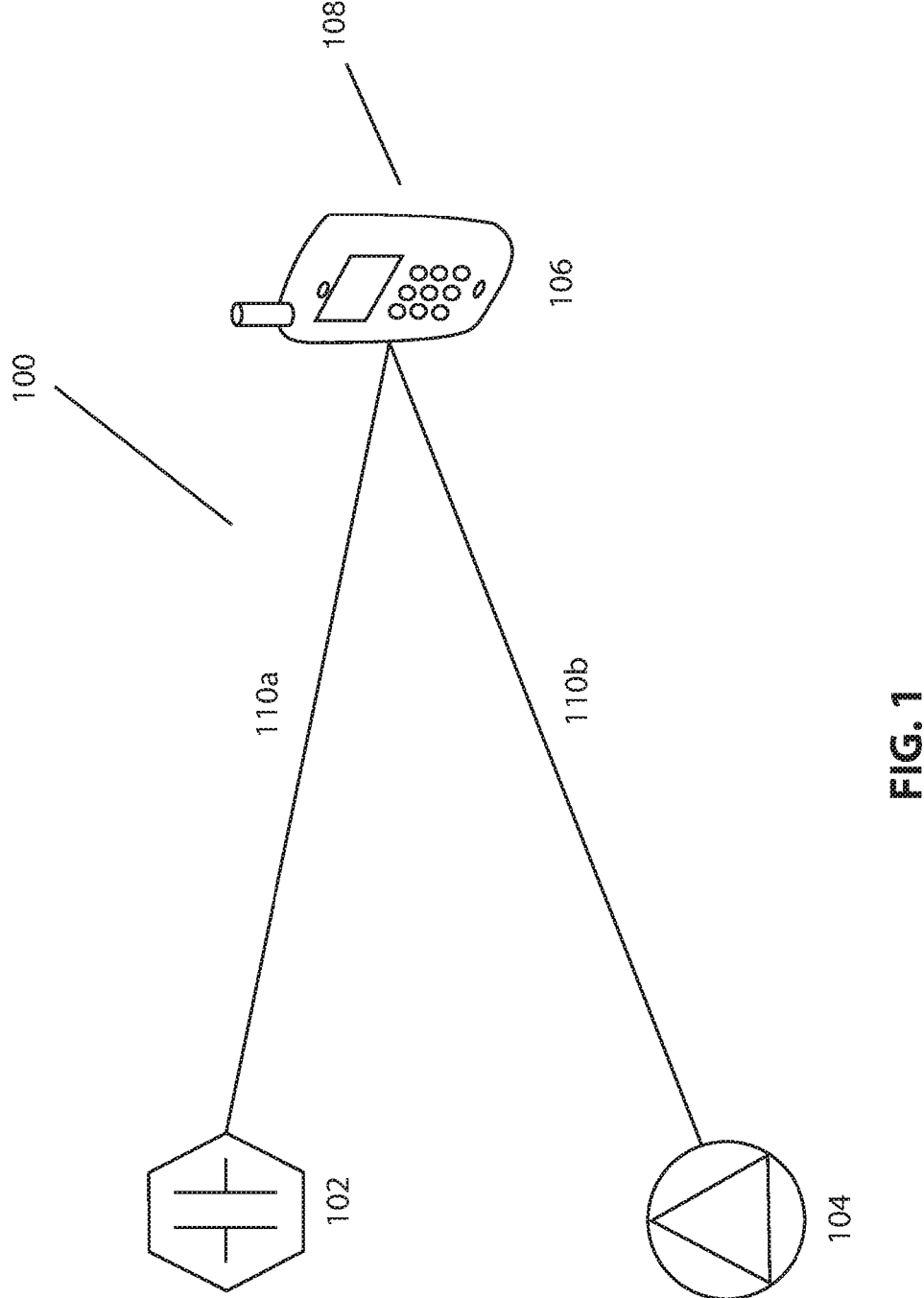
FIG. 1 is a schematic view of an exemplary system adapted to implement one or more of the techniques disclosed herein.

FIG. 1 is a schematic view of an exemplary system 100 adapted to implement one or more of the techniques disclosed herein.

The illustrated system 100 includes a glucose monitoring/measuring device 102, an insulin delivery device such as a pump 104, and a controller 106. The controller 106 has a user interface 108, an internal computer-based processor and internal computer-based memory storage capacity.

In a typical implementation, the insulin pump 104 is adapted to deliver insulin to a user (e.g., a person with diabetes) according to a non-discretionary insulin delivery schedule. The non-discretionary insulin delivery schedule is non-discretionary because insulin will be delivered according to what the schedule indicates, regardless of what the user's actual blood glucose levels are and regardless of how much insulin already has been delivered to the user.

As used herein, a "user" is typically a person who receives insulin from the inventive devices, systems and methods disclosed herein. In some implementations, actions may be performed by a "caregiver" who is a person or persons different from the "user." For example, the caregiver may be a parent, other family member, teacher, physician, clinician, advisor, or other person(s) assisting the user with management of his or her diabetes. In some implementations, actions ascribed to a caregiver must be performed by the caregiver(s) and may not be performed by the user. In other implementations, the user and the caregiver are one and the same person, and there is no other person directly involved in the delivery of insulin to the user.

Non-discretionary insulin delivery may include a constant infusion, basal rates; point in time bolus delivery and; fixed rate bolus delivery over a set period of time. The various non-discretionary insulin delivery programs may be combined by the user in virtually any combination. This delivery is non-discretionary in that once the user or caregiver requests the insulin delivery; the delivery will happen regardless of the user's blood glucose levels and regardless of how much insulin has already been delivered to the user. In some implementations, the only way a user's non-discretionary delivery is changed is if the user or a caregiver takes an action to change the pre-defined delivery. Thus, we define non-discretionary delivery in these implementations as insulin delivery that is determined solely by the user or a caregiver and where there is no discretion left to the insulin pump control system as to whether to give more or less than the user or caregiver has requested or programmed.

Additionally, in a typical implementation, the system 100 is adapted to facilitate delivery of insulin to the user on a discretionary basis. In this regard, the system 100 is able to deliver insulin to the user on an "as needed" basis within parameters defined by the user or caregiver. A discretionary insulin delivery is a permissible but not mandatory delivery of insulin and is automatically delivered (i.e., without further involvement from the user or caregiver) to the user if the system determines that such a delivery is warranted (i.e., such a delivery would be helpful to the user) and is not otherwise constrained from implementing the discretionary delivery.

A discretionary delivery of insulin can be in addition to whatever insulin is being delivered according to the non-discretionary insulin delivery schedule, or in lieu of some or all of the insulin that would have been delivered according to the non-discretionary insulin delivery schedule.

For example, a discretionary delivery could allow varying the pre-programmed basal rate of z units per hour to a basal rate between x units per hour and y units per hour. In this case, the discretionary delivery would be in lieu of the non-discretionary basal delivery. That is, during the time of the discretionary delivery, the pre-programmed constant basal rate of z units per hour would be replaced by the discretionary delivery that could vary between x and y units per hour. The system may constantly adjust this rate of delivery based on a variety of factors. Z would typically be contained in the range defined by x and y but there may be situations where it lies outside of that range.

A discretionary delivery may also be requested in addition to a non-discretionary delivery program. For example, a system may allow a discretionary bolus where the user defines a minimum and maximum amount of insulin to be delivered over a certain time period. In a situation where a user eats a meal that requires between 3 and 6 units of insulin, this type of bolus could be very helpful to the user. In this scenario, the user or caregiver could program a discretionary bolus with minimum 3 units and maximum 6 units of insulin to be delivered over some amount of time determined by the user. In this way, the user may let the system manage the uncertainty associated with how much insulin is actually required. In this example, the discretionary delivery is in addition to the non-discretionary basal rate delivery previously programmed by the user.

In this regard, the system 100 is adapted to enable the user or caregiver to specify parameters associated with the discretionary insulin delivery. The parameters may define one or more time periods within which a discretionary insulin delivery may occur. The parameters also may specify a maximum amount of insulin, a maximum rate of insulin delivery, a minimum amount of insulin, a minimum rate of insulin delivery, etc., for one or more (or all) of the specified time periods. The parameters may specify whether the discretionary delivery, if deemed warranted, should be in addition to any insulin being delivered according to the non-discretionary insulin delivery schedule, or in lieu of some or all of the insulin that otherwise would have been delivered according to the non-discretionary insulin delivery schedule.

The exemplary system 100 is also adapted to determine, during any periods of time, that a discretionary insulin delivery may occur, whether a discretionary insulin delivery is warranted (i.e., whether a discretionary insulin delivery would likely help the user). In a typical implementation, this determination is made on a rolling basis. In one implementation, for example, a new determination is made every five minutes, based on any information received in a four-hour time window immediately preceding the time that the new determination is made.

The determination of whether a discretionary delivery is warranted can be made based on various information including, for example, the user's blood glucose level over time and an estimate of how much insulin-on-board (IOB) is in the user's body.

In general, the user's IOB represents an amount of insulin that has already been delivered to the user but has yet to act on the user's blood glucose level. In a typical implementation, the system 100 can estimate IOB for the user based on information about recent actual insulin deliveries from the insulin pump 104 and insulin absorption information (e.g., the user's insulin absorption curve, the user's duration of insulin action (DIA), which defines how long it takes for 100% absorption, etc.) that may be specific to the user.

Traditional insulin-on-board calculations typically do not include basal rate insulin deliveries. Such basal deliveries typically are intended to merely maintain the current blood glucose level, not to raise or lower it, and not to offset the effect of a meal, etc., as does a bolus delivery. However, as used herein, the calculation of insulin-on-board may include some or all of the following: non-discretionary meal related bolus insulin; non-discretionary correction related bolus insulin; non-discretionary extended bolus delivery; non-discretionary basal insulin delivery; and insulin delivered as part of a discretionary delivery request.

Insulin on board for a point delivery of insulin (such as a bolus) may be determined by multiplying the amount of the insulin delivery by the percentage of absorption remaining as determined by the time since the delivery, the absorption curve and the DIA. A typical absorption curve will define a percentage of insulin remaining on the y-axis by the time since bolus on the x-axis.

To calculate insulin on board for a continuous delivery of insulin such as a basal delivery or an extended bolus, the continuous delivery of insulin may be discretized into very small bolus deliveries of insulin. For example, if a basal rate is 1 unit per hour and we would like to calculate the insulin on board from 1 hour of such a basal rate, we could discretize the basal delivery into 60 boluses of ⅟₆₀th of a unit, delivered at minute 1, 2, 3, . . . , 60 of the hour. Once discretized, the IOB for each individual discretized bolus may be calculated as described above, and then summed together to compute the IOB for the entire continuous delivery.

The insulin on board for a discretionary delivery that is in addition to a non-discretionary delivery may be calculated in the same manner as a non-discretionary delivery. That is, any point deliveries of the discretionary delivery may be calculated as if it were a bolus. A continuous discretionary delivery may be calculated by following the discretization method described above.

In some implementations, it may be beneficial to calculate the IOB of a discretionary delivery by calculating it relative to the non-discretionary delivery that the discretionary delivery replaced. For example, take a discretionary delivery that allows the basal rate to vary between x and y units per hour in lieu of the pre-programmed z units per hour. In some implementations, the IOB for the discretionary delivery may be calculated by computing the IOB for both the discretionary delivery (IOB_discretionary) and for the non-discretionary delivery that it replaced (IOB_non-discretionary) and then taking the difference, IOB_discretionary—IOB_non-discretionary to find the IOB to assign to the period of the discretionary delivery. Note that in cases where the IOB_discretionary is less than the IOB_non-discretionary, the IOB calculated for such discretionary delivery period is negative. A negative IOB may be added to any other IOB from other deliveries (positive or negative) in a simple additive manner to calculate the total IOB for the user.

A negative IOB reflects that the user has received less insulin than the pre-programmed, non-discretionary delivery would have delivered. Since standard insulin therapy provides for the pre-programmed basal delivery to keep glucose values at static levels, the delivery of less than the pre-programmed basal rate results in a deficit of insulin relative to what the user would need to keep glucose levels static. This deficit results in an expected subsequent rise in glucose values equal to the absolute value of the insulin deficit amount multiplied by the user's insulin sensitivity factor (ISF).

In some implementations, the benefit of computing the IOB of a discretionary delivery on a relative basis is that it allows the user or caregiver to more easily understand what the net effect is of the therapy changes from the discretionary delivery. Depending on the implementation, the discretionary delivery may deliver more or less than the non-discretionary, pre-programmed delivery schedule. The relative IOB calculation allows the user to see if the net effect of the discretionary delivery is an increase (positive IOB) or decrease (negative IOB) to the standard, pre-programmed delivery schedule.

If a discretionary delivery of insulin is warranted, the system 100 is further adapted to determine how much discretionary insulin should be delivered and when exactly it should be delivered. In this regard, the system 100 may be programmed with logic to make these decisions based on a variety of information, such as the user's current or predicted blood glucose level, IOB level, etc. Moreover, the system 100 may be guided in these decisions by the parameters specified by the user in authorizing the discretionary delivery and/or other system delivery constraints.

In general, authorizing a discretionary insulin delivery gives the system 100 some flexibility in administering insulin to the user. This can be advantageous in a number of situations. For example, if the user or caregiver is unsure about what effect eating a particular meal might have on the user's blood glucose level, that person might authorize a discretionary insulin delivery to give the system 100 a better chance of managing any unpredicted swings in blood glucose.

Moreover, since the user or caregiver is able to set the parameters associated with any discretionary delivery, there is an inherent degree of safety built-in to the system 100. This is because the user or caregiver would not likely specify parameters that might result in harm. In some implementations, there is one or more additional safety measures built into the system as well.

One of those additional safety measures, for example, may be the system 100 having certain delivery constraints. In general, a delivery constraint may be considered a hard limit on discretionary insulin delivery that the system 100 cannot violate under any circumstances. So, even if the system 100 were to determine that a particular discretionary insulin delivery was warranted, if that discretionary delivery would result in one or more of the delivery constraints being violated, then the discretionary delivery would not be delivered, or at least would be truncated so as to not violate any delivery constraints.

Some exemplary delivery constraints include: that a particular amount of insulin must be delivered over or within a particular minimum or maximum length of time; that a rate of insulin delivery must not exceed some specified maximum rate; that an amount of insulin delivery during a particular length of time must not exceed a specified maximum amount; that the rate of insulin delivery at any point in time must be at least a specified minimum; that an amount of insulin delivered during a particular window of time must be at least a specified minimum amount, etc.

Moreover, in situations where the system 100 is considering whether to add insulin, the system 100 may constrain delivery of discretionary insulin to the user, even if the system 100 otherwise determines that some amount of discretionary insulin would be appropriate to be delivered to the user, if one or more criteria have been satisfied. These criteria can include, for example, if IOB−(current bg−target bg)/(C_1*ISF)−C_2>0, or if more than a fixed amount of insulin has been delivered in the past N hours or minutes (or any unit of time), where IOB represents insulin-on-board, and ISF represents an insulin sensitivity factor, and C_1 and C_2 are constants defined by the user and in some implementations C_2 is a function of the preprogrammed basal rate. In some cases, C_2 may be a fixed amount of insulin while in others it may be a function of a current or future preprogrammed basal rate. C_2 may be either positive or negative with a negative value creating a more conservative dosing approach.

Other implementations may constrain the discretionary delivery when the IOB is large when compared to the spread between the recent bg and the target bg range. The spread between the recent bg and the target bg may be a simple difference, a difference of the logarithms of the two values or virtually any function of the two values that increases as the recent bg increases and moves away from the target range.

There may additionally be constraints for a discretionary delivery that require that the most recent glucose level is above (or below) a threshold in order to augment (or attenuate) the non-discretionary delivery program it replaces.

An additional safety measure that may be included in certain implementations is an alarm. The alarm may be incorporated into the controller 106, for example. The alarm can be an audible, visual and/or tactile.

The alarm can be adapted to trigger in response to various possible conditions including, for example, when the user's blood glucose level passes certain threshold values or when the amount of insulin that has been delivered as part of a discretionary delivery exceeds some threshold value. For example, the alarm might trigger if all of the insulin that has been authorized for discretionary delivery during a particular period of time has been delivered to the user. If an alarm occurs, the system 100 is generally adapted to indicate to the user and/or caregiver what condition or conditions triggered the alarm. Moreover, the system 100 typically is adapted to enable the user or caregiver to acknowledge a triggered alarm.

In some implementations, if the alarm triggers because the system 100 has delivered a prescribed maximum amount of discretionary insulin to the user in a given time period, then the person's acknowledgement of the alarm may be considered a verification by the system that the person considers this maximum delivery to be acceptable.

In some implementations, the alarm may trigger based on a weighted sum of insulin delivered over a given time period. In this case, a weight may be assigned to every sub-period of time, such as every five minutes. Typically, the weights would be a function of how long in the past from the current time the sub-period is. A simple weighting scheme, as noted above, would involve using a weight of 1 for all sub-periods in a given time period and 0 for all sub-periods prior. In some implementations, a more complex weighting scheme may include using an exponential decay function to assign a greater weight to more recent sub-periods. Such a weighting scheme could assign a value of e^(−alpha*period) where period is the number of sub-periods back from the current time and alpha is some positive real number. For example, if the sub-periods are five-minutes long, then a value for alpha of 0.03 would be a reasonable value in some implementations. Other implementations may use arbitrary weighting schemes that may relate to the absorption profile of the insulin or virtually any function that seems appropriate.

Another method for triggering an alarm would entail independently examining the amount of dosing in each sub-period over a given period. Each sub-period may then be assigned a certain value based on whether insulin was augmented or attenuated during the sub-period. This sub-period-value may be a function of how much the insulin was increased or decreased during the sub-period or it may be a simple 1, 0, −1 for whether the insulin was augmented, unchanged, or attenuated, respectively. In some implementations, the system is only interested in sub-periods when insulin is augmented and thus could use a function that assigns a 1 to any sub-period where insulin was increased and a 0 to all other sub-periods. These exemplary systems represent a small fraction of the possible sub-period-value-functions that may suit different implementations. Once the values for each sub-period have been determined they may be summed in a weighted fashion, as described above, to come up with a metric on which an alarm may be based.

For example, one implementation of this type of alarm would be for the system to terminate discretionary insulin delivery if more than 80% of the 5 minute periods during the past 3 hours have resulted in the a discretionary insulin delivery greater than the non-discretionary program would have delivered. This alarm may be independent and irrespective of whether the total amount of insulin delivered is greater than a pre-determined maximum dosing amount. If such an alarm goes off, then the actual amount of discretionary insulin delivered during the given time period may be considered to be the maximum-discretionary-amount for the purposes of subsequent attenuation described below.

In some implementations, if the person does not acknowledge the alarm in a timely manner (e.g., because he or she is sleeping or otherwise unconscious), then the system 100 will automatically reduce (i.e., without input from the person) the amount of insulin to be delivered in a period of time following the person's failure to acknowledge the alarm. Typically, this reduction of insulin delivery in the period following the person's failure to acknowledge the maximum-discretionary-delivery alarm is intended to at least partially offset what could potentially have been an over-dosage of insulin resulting from a discretionary delivery. In some implementations, under these circumstances, the system 100 reduces the amount and rate of insulin delivery to zero for such period until the difference between the amount of insulin the non-discretionary delivery schedule would have delivered equals the prescribed maximum discretionary amount of insulin that was previously delivered. In other implementations, under these circumstances, the reduction in subsequent non-discretionary delivery would equal the difference between the prescribed maximum discretionary delivery schedule and the non-discretionary delivery that would have occurred during the time period of the discretionary delivery. In these scenarios, the non-discretionary delivery schedule would subsequently resume at the end of such period.

Typically, the alarm functionality addresses a concern that the continuous glucose monitor 102 readings that may help determine discretionary insulin deliveries may be inaccurate for some period of time resulting in a sub-optimal excessive dosing of insulin to the user. In some implementations, the alarm functionality can mitigate (or alleviate) some concerns and problems associated with such occurrences. When the discretionary delivery reaches a maximum authorized dose, for example, the person is alerted that he or she should verify that the dosing was appropriate and, if not, take preventive action to offset the unnecessary insulin dosing with carbohydrates before the insulin potentially dangerously lowers blood glucose levels. In the event that the user or caregiver is unable to acknowledge the alert due to unconsciousness or sleep, the system 100 automatically takes corrective action to ameliorate potential negative effects of excessive-dosing.

In some implementations, the system 100 determines whether to make a discretionary delivery of insulin based on information from the continuous glucose meter 102 regarding the user's blood glucose levels. If, for example, the information provided by the continuous glucose meter 102 to help the system 100 make a determination in this regard was inaccurate, then it is possible that the user may have improperly received an excessive dose of insulin. Under those circumstances, and if the person does not acknowledge the resulting alarm (e.g., due to being asleep, etc.), then the system 100 will take corrective action automatically.

In the illustrated implementation, the glucose monitoring/ measuring device 102, the insulin pump 104, and the controller 106 are configured so that they can communicate with each other using wireless communication channels 110*a*, 110*b* (e.g., using wireless communication technologies). However, in other implementations, information may be transferred between the components illustrated in FIG. 1 using a wired connection or may, in some instances, be transferred by the user or caregiver him or herself. For example, if the glucose measuring/monitoring device 102 is a monitor that simply presents the blood glucose reading on a visual display, for example, but is not able to transmit the reading directly to the controller 106, then the person using the system 100 may view the displayed blood glucose reading and enter that reading manually at the controller 106. In other implementations (not shown), any one of the glucose monitoring/measuring device 102, the insulin pump 104 and the controller 106 can be combined with another of the devices in a single integrated unit, or all three may be combined. In combined devices, discretionary delivery protocols may be provided by a dedicated computer-based processor, or a single processor may control discretionary delivery protocols, glucose monitoring, insulin delivery device functions and/or user interface functions.

In various implementations, the glucose monitoring/measuring device 102 can be a continuous glucose monitor, a blood glucose meter, an intravenous blood glucose measurement device, or other device adapted to provide an indication of blood glucose levels in the user. In some implementations, the level of glucose in the user's blood may never be directly measured. Rather, the glucose level in the user's interstitial fluid or other bodily fluid or tissue may be measured, and at some point may (or may not) be converted into an equivalent glucose level of whole blood, plasma or serum. It is to be understood that the use herein of the terminology "blood glucose" level may mean actual blood glucose level or a surrogate glucose level, depending on the context.

The insulin "pump" 104 can be any type of insulin delivery device. In general, the insulin pump is a medical device used for the administration of insulin, for example, in the treatment of diabetes. The pump can have a variety of possible configurations. In some implementations, for example, the insulin pump 104 includes a pump (with controls, processing module, batteries, etc.), a disposable reservoir for insulin (which may be inside the pump), and a disposable infusion set, including a cannula for subcutaneous insertion (under the skin) and a tubing system to interface the insulin reservoir to the cannula. In some implementations, however, the pump may not include one or more of these components. For example, in some implementations, the pump will not have tubing. Also, in some implementations, the pump will not include a disposable reservoir. In other configurations, the pump may be controlled by a handheld device or by an application loaded onto a mobile phone or other mobile computing device. It is to be understood that, depending on the context, the use herein of the terminology "pump" or "delivery device" may refer to conventional insulin pumps available on the market today, or may refer to other insulin delivery devices such as insulin pens, automated inhalers, variable rate insulin skin patches and other such delivery devices, whether or not they are commercially available today. It is envisioned that the devices, systems and methods disclosed herein may also be applied to other insulin delivery methods, such as intravenous insulin delivery in an intensive care unit, and may also find use in delivering other medicines or fluids to a user. In such other systems, analyte(s) other than glucose may be monitored in a user's body to aid in determining the desired amount of medicine or fluid to be delivered to the user.

The controller 106 can be any type of computer-based device configured to implement and/or facilitate the functionalities disclosed herein. In some implementations, the controller 106 is a smartphone executing the ANDROID® operating system. However, the controller 106 can be any type of smartphone (or other device) executing any type of operating system. In general, a smartphone is a mobile phone built on a mobile operating system, with more advanced computing capability connectivity than a feature phone. Many modern smartphones also include high-resolution touchscreens and web browsers that display web pages. High-speed data access can be provided by Wi-Fi and/or mobile broadband.

Although shown as three separate components, the controller 106 and/or certain of its functionalities described herein can be physically integrated into the glucose monitoring/measuring device 102 and/or the insulin pump 104.

Figure 2:
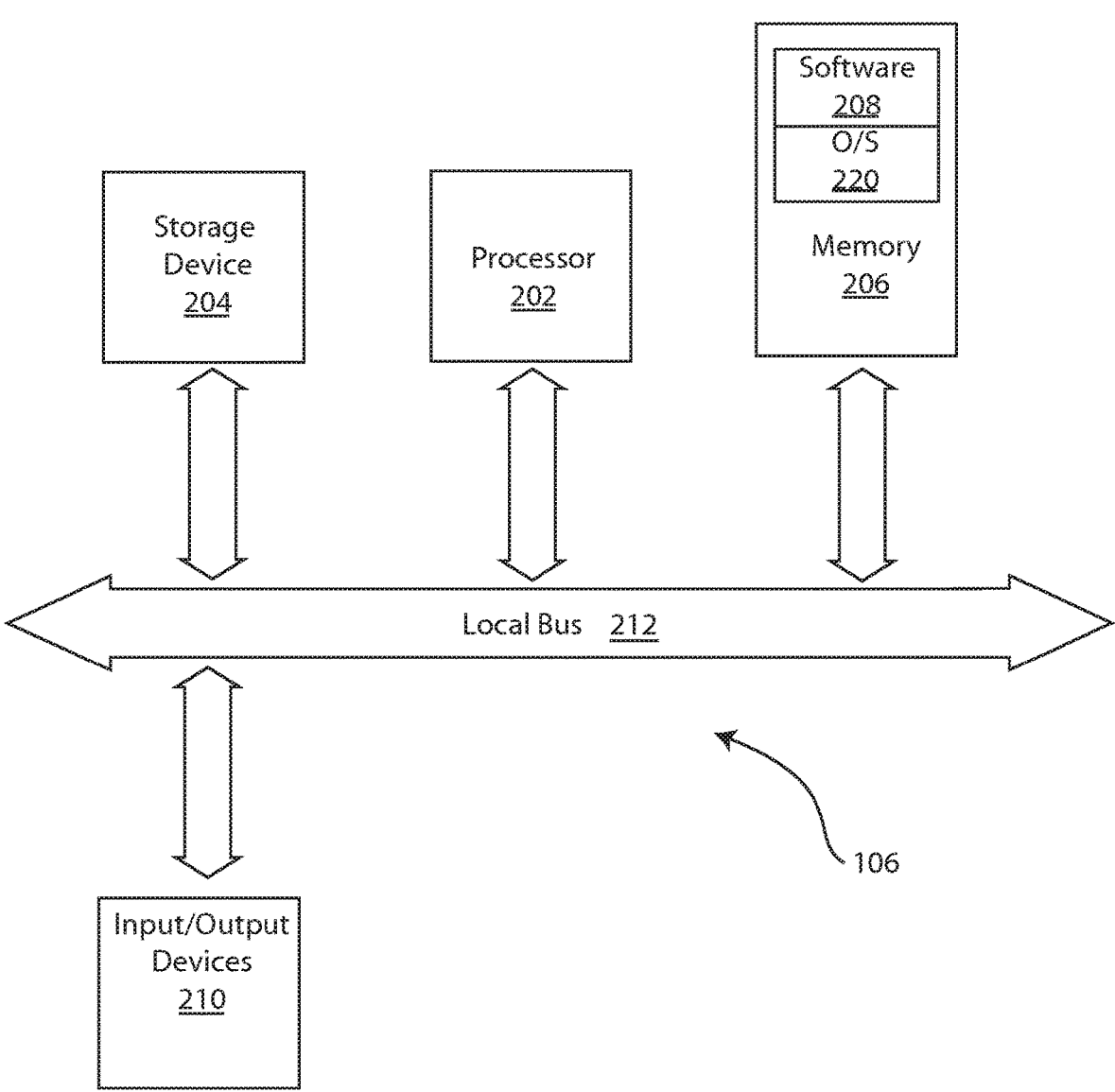
FIG. 2 is a schematic diagram illustrating an example of the controller in FIG. 1.

FIG. 2 is a schematic diagram illustrating an exemplary configuration of the controller 106.

The illustrated controller 106 has a processor 202, a storage device 204, a memory 206 having software 208 stored therein that defines certain aspects of the functionality disclosed herein, input and output (I/O) devices 210 (or peripherals), and a local bus or local interface 212 allowing for communication among the various components within the controller 106. The local interface 212 can be, for example, one or more buses or other wired or wireless connections. The local interface 212 may have additional elements, which are omitted for simplicity, such as controllers, buffers (caches), drivers, repeaters, and receivers, to enable communications. Further, the local interface 212 may include address, control, and/or data connections to enable appropriate communications among the aforementioned components.

The processor 202 is a hardware device for executing software, for example, software 208 that is stored in the memory 206. The processor 202 can be any custom made or commercially available single core or multi-core processor, a central processing unit (CPU), an auxiliary processor among several processors associated with the controller 106, a semiconductor based microprocessor (in the form of a microchip or chip set), a macroprocessor, or generally any device for executing software instructions. For example, if the controller 106 is an APPLE® iPʜᴏɴᴇ® 5 smartphone, then the processor 202 may be an APPLE® A6 APL0589, Dual Core 1.2 GHz processor.

The memory 206 can include any one or combination of volatile memory elements (e.g., random access memory (RAM, such as DRAM, SRAM, SDRAM, etc.)) and non-volatile memory elements (e.g., ROM, hard drive, tape, CD-ROM, etc.). Moreover, the memory 206 may incorporate electronic, magnetic, optical, and/or other types of storage media. The memory 206 can have a distributed architecture, where various components are situated remotely from one another, but can be accessed by the processor 202.

In general, the software 208 defines one or more functionalities that may be performed by the controller 106. The software 208 in the memory 206 may include one or more separate programs, each of which contains an ordered listing of executable instructions for implementing logical functions of the controller 106. The memory 206 may contain the operating system (O/S) 220. The operating system 220 essentially controls the execution of programs within the controller 106 and provides scheduling, input-output control, file and data management, memory management, communication control, and related services.

The I/O devices 210 may include input devices, such as a keyboard, mouse, scanner, touchscreen, microphone, roller ball, etc. Furthermore, the I/O devices 210 may also include output devices, such as a display, an audio speaker, a vibrator, etc. Finally, the I/O devices 210 may further include devices that operate as both input and output devices, such as a modulator/demodulator (modem; for accessing another device, system, or network), a radio frequency (RF) or other type of transceiver, a telephonic interface, a bridge, a router, or other device/component (e.g., one or more interface units).

In general, when the controller 106 is in operation, the processor 202 executes software 208 stored in the memory 206, communicates data to and from the memory 206, and generally directs operations of the controller 106.

Figure 3:
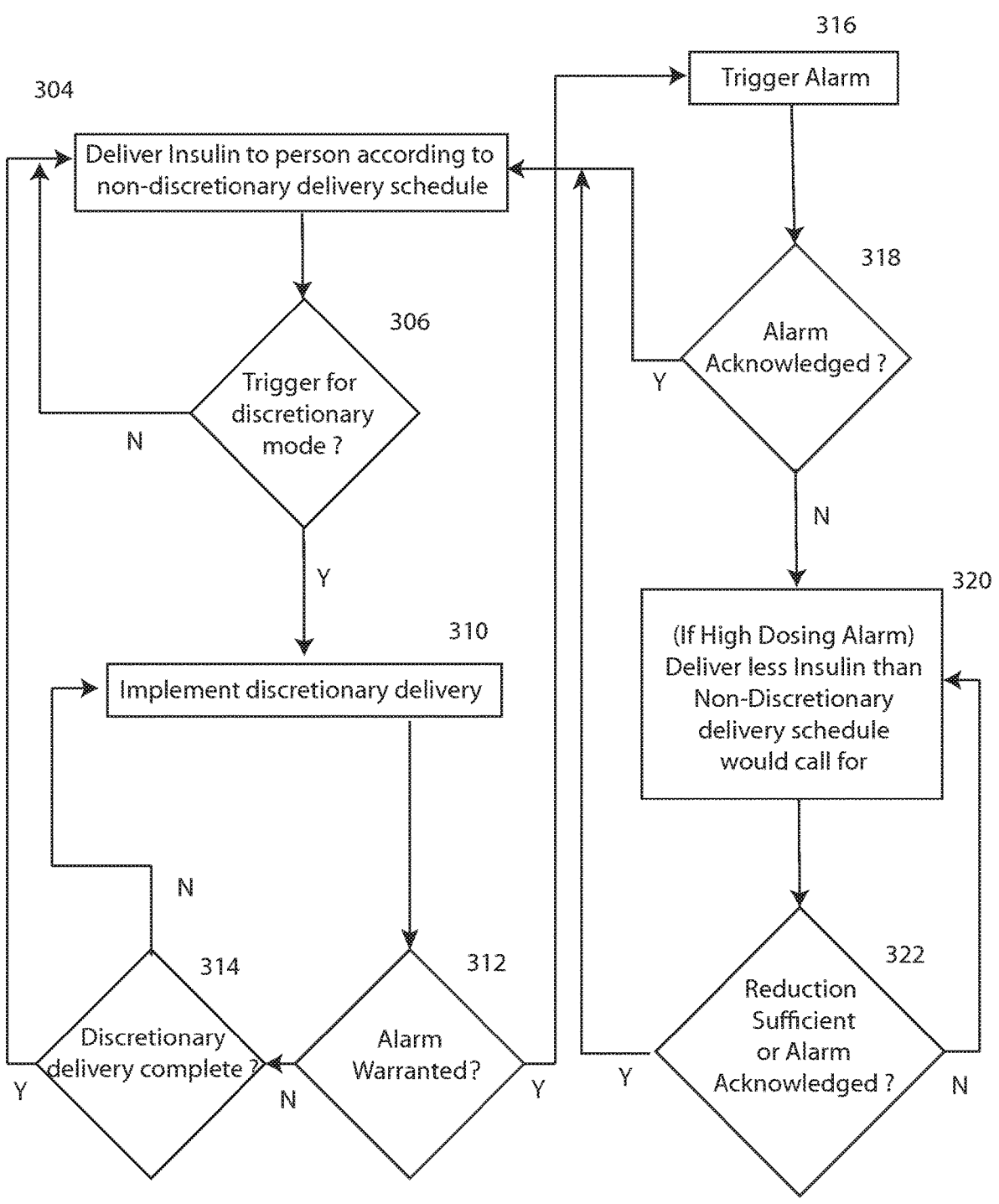
FIG. 3 is a flowchart showing one implementation of a method that includes facilitating a discretionary delivery of insulin to a user.

FIG. 3 is a flowchart showing one implementation of facilitating delivery of insulin to a user. The illustrated method may be implemented by the system 100 represented in FIGS. 1 and 2 and described herein.

In a typical implementation, the system 100 enables a person (e.g., a user) to specify parameters associated with a discretionary delivery of insulin that may be delivered to the user. In some implementations, the system 100 enables the user or caregiver to specify these parameters by enabling the person to enter information at a user interface (e.g., by using the display screen and/or a keypad at the controller 106).

Figure 5:
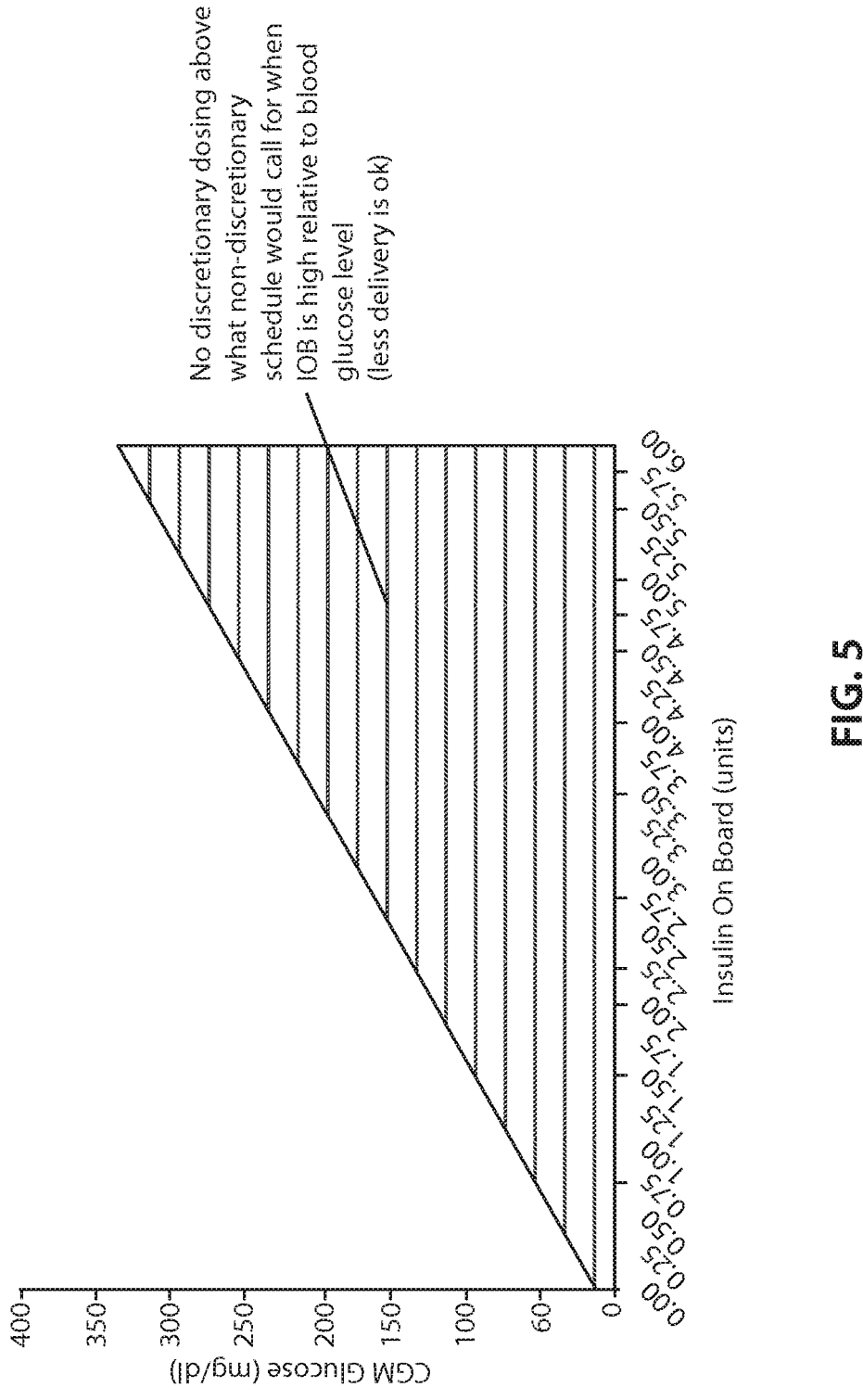
FIG. 5 is a plot of blood glucose versus insulin-on-board.

So, for example, the system 100 may present to the person at the display screen of the controller 106, a selectable icon that provides the person with access to an interaction that enables the person to specify these parameters. The parameters may identify, for example, one or more specific time periods during which the system 100 will be authorized to make a discretionary insulin delivery, if warranted. In addition, the parameters may identify various other aspects of the discretionary delivery authorization. For example, in various implementations, the system may enable or prompt the person to specify parameters that authorize discretionary insulin deliveries of:

up to X units in T hours (with no constraint on rate of delivery);

between X and Y units delivered in T hours (with no constraint on rate of delivery) between X and Y units in T hours with a delivery rate constrained between A units/hour and B units/hour (note: A may or may not equal 0);

between X and Y units in T hours with a delivery rate between A units/hour and B units/hour and where X=[non-discretionary delivery over time T]−M and Y=[non-discretionary delivery over time T]+N (this is an example of #3 where X and Y are functions of the non-discretionary delivery schedule);

iteratively perform #4 periodically (e.g., every 5 minutes) evaluating based on the prior T hours;

if the discretionary delivery algorithm reaches the constraint of a delivery equaling X or Y units of insulin during any T hour period, then the discretionary delivery would end, non-discretionary delivery would resume and an alarm and/or notification may be sounded to alert the user/caregiver;

in the case of 6, where the maximum Y units of insulin have been delivered, if the person does not acknowledge the alarm within a predetermined amount of time (e.g., 5 minutes) then the system may attenuate subsequent non-discretionary delivery of insulin for some amount of time to offset some or all of the discretionary insulin delivery. This offset amount, in some cases, may be equal to the difference between the discretionary delivery and the non-discretionary delivery that the discretionary delivery replaced;

no discretionary dosing over and above what the non-discretionary delivery schedule calls for if the relative level of a user's glucose level to insulin-on-board is below a particular value (see FIG. 5);

if the fraction of D minute sub-periods where more than C units of insulin are delivered during a T hour period exceeds a constraint F, then the discretionary delivery would end, non-discretionary delivery would resume and an alarm and/or notification may be sounded to alert the person (C may be a constant or a function of the non-discretionary basal rate for each sub-period); and/or in the case of 9, where the alarm is triggered, if the person does not acknowledge the alarm within a predetermined amount of time (e.g., 5 minutes) then the system may attenuate subsequent non-discretionary delivery of insulin for some amount of time to offset some or all of the discretionary insulin delivery. This offset amount, in some cases, may be equal to the difference between the discretionary delivery and the non-discretionary delivery that the discretionary delivery replaced.

In the scenarios set forth above, X, Y, T, A, B, C, D, M and N are variables that can represent virtually any positive number or zero. F represents a number between zero and one.

In some implementations, the system 100 enables (e.g., prompts) the user to specify other parameters or combinations of these and/or other parameters as well. The parameters can authorize discretionary delivery of insulin in terms of one or more basal rates, one or more boluses or combinations thereof.

Typically, the person is able to specify the parameters of a discretionary delivery anytime (e.g., just before triggering discretionary delivery mode, or any other time).

In a typical implementation, the system 100 stores any parameters specified by the person, for example, in the memory device 206 of the controller 106.

According to the illustrated implementation, the system 100 delivers (at 304) insulin to the user according to a non-discretionary delivery schedule.

In general, the phrase "non-discretionary delivery schedule" refers to a schedule that does not allow the system 100 to exercise any discretion in delivering insulin to the user. So, for example, a typical non-discretionary delivery schedule might include a preprogrammed schedule for delivering insulin to a user over the course of a day (e.g., 1 unit per hour, all day long) or longer as well as any variations from that schedule (e.g., deliver 1 unit as a bolus at 3 p.m. or non-discretionary extended boluses) that the person instructs must happen. When operating according to a non-discretionary delivery schedule, the system 100 is not permitted to exercise any discretion in delivering insulin to the user. It merely delivers an amount of insulin that is dictated by non-discretionary delivery schedule.

In the absence of a trigger (e.g., at 306 in FIG. 3) to enter a discretionary delivery mode, the system 100 simply continues (at 304) to deliver insulin to the user according to the non-discretionary delivery schedule.

However, if a trigger does occur (at 306), then, according to the illustrated implementation, the processor 202 causes the system 100 to implement (at 310) a discretionary delivery of insulin. In some implementations, the insulin delivered pursuant to the discretionary delivery is in addition to any insulin delivered pursuant to the non-discretionary delivery schedule if the non-discretionary delivery is not suspended in response to the trigger. In some implementations, the insulin delivered pursuant to the discretionary delivery is in lieu of some or all of the insulin that would have been delivered pursuant to the non-discretionary delivery schedule, if the non-discretionary delivery is suspended in response to the trigger.

The trigger (at 306) can be virtually any kind of trigger. For example, in some instances, the trigger may come from the person pressing a button at the controller 106 to initiate a discretionary delivery. In some instances, the trigger may come from a timer indicating that a designated period of time where discretionary delivery is authorized (e.g., 9:00 p.m. to 6:00 a.m.) has begun. In some instances, the trigger may come from the user's blood glucose readings reaching a certain value. In some instances, the trigger may relate to an amount of insulin that has been or soon will be delivered to the user. In some instances, the trigger may be in response to the person pressing a button indicating that a meal is taking place or about to take place. The trigger may also be based on the location of the user which may be ascertained by an internal GPS system or by virtue of being within wireless connectivity of a certain location based device (such as a BLUETOOTH® device or a Wi-Fi device).

The data that may cause the trigger can come from a variety of different sources. For example, the user's blood glucose readings may come from the glucose monitoring device 102 or may be entered by the user directly into the controller 106 via its user interface. The amount of insulin that has been delivered to the user may come from the insulin pump 104. The amount of insulin that soon will be delivered to the user can come from the non-discretionary delivery schedule that may reside, for example, on the insulin pump 104 and/or in the controller 106. The person's button press (or the like) may come from the controller 106 or from the insulin pump 104. The radio signal to determine a location may come from a wireless access point or a BLUETOOTH® device.

Some of this data e.g., the data that comes from the insulin pump 104 or the glucose monitoring device 102, may travel to the controller 106 (i.e., the processor 202 in the controller 106) via the respective wireless communication channels 110*b*, 110*a*. In some implementations, at least some of this data (e.g., blood glucose readings) is transmitted to the processor 202 on a continuous, substantially continuous, periodic or occasional basis.

As part of implementing the discretionary delivery (at 310), the system 100 determines an amount of discretionary insulin and, in some implementations, a precise time when that discretionary insulin should be delivered to the user.

One way that the system 100 (e.g., the processor 202) might make these kinds of determinations is by the processor 202 in the controller 106 determining whether the user's blood glucose level will, at some future point in time, likely move outside a range of acceptable blood glucose levels.

Figure 7:
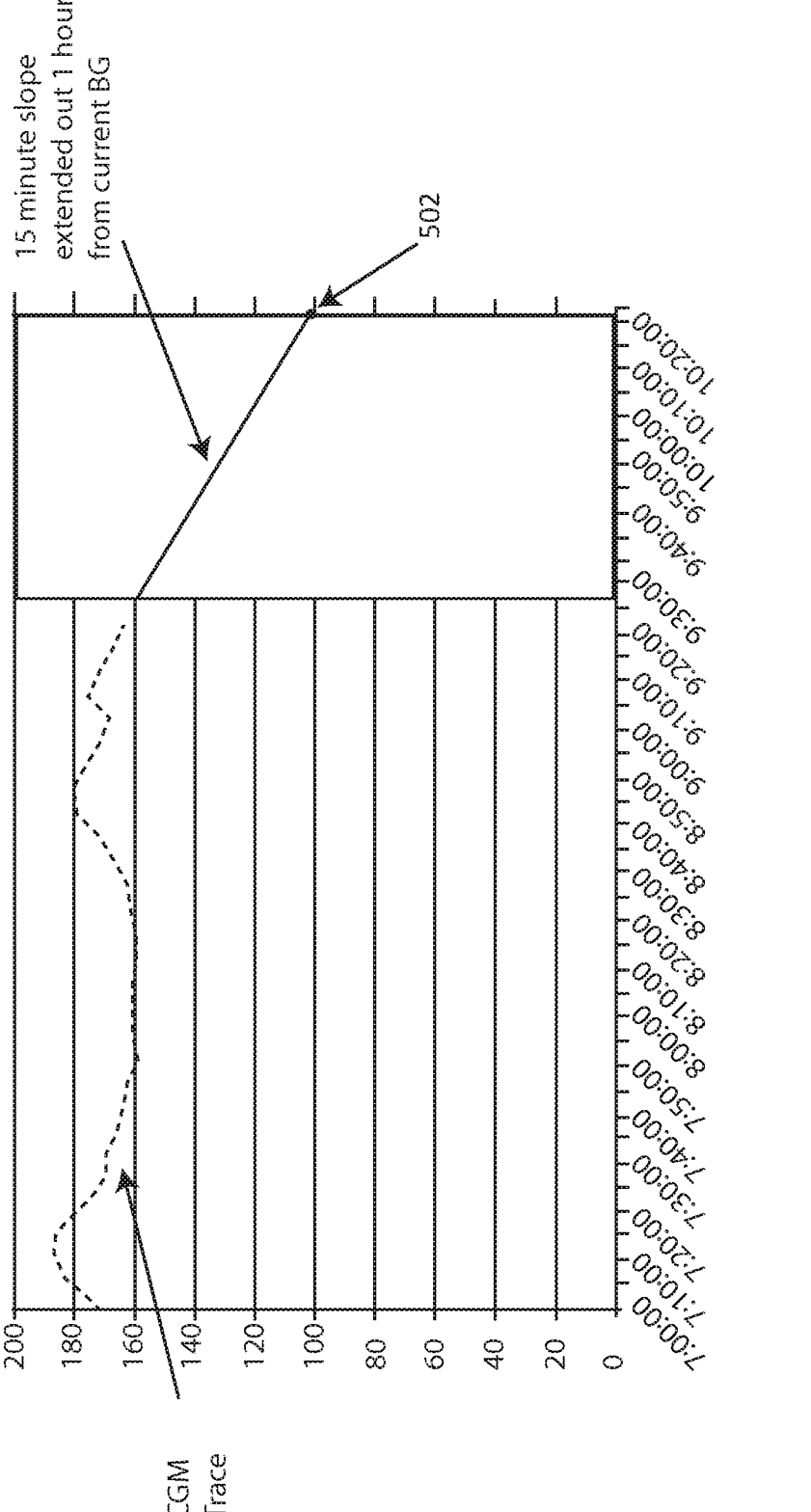
FIG. 7 is a time plot showing blood glucose readings and a projected blood glucose level.

In this regard, the graph in FIG. 7 shows a user's recent blood glucose readings plotted against time. The graph shows that the user's blood glucose level went up and down from the first reading in the graph, taken at 7:00:00, until the last reading in the graph, taken at 9:30:00. In the illustrated example, a new reading was taken approximately every five minutes. The last five readings in the illustrated graph show a gradual downward slope of the user's blood glucose levels. The period beyond 9:30:00 in the illustrated graph represents the future.

In some implementations, in order to determine whether the user will likely benefit from a discretionary insulin delivery, the processor 202 may project out into the future (represented by the future region in the illustrated graph) a continuation of whatever trend (e.g., slope) a most recent set of blood glucose readings (e.g., 3, 4, 5 or more readings) indicate.

In the illustrated example, the most recent set of readings (e.g., looking back about 15 minutes from the last reading in the illustrated example) indicate a downward slope that, if projected out 1 hour into the future, would result in a blood glucose level indicated by point 502. The 1 hour projection into the future is represented in the illustrated example by a straight, solid line that extends from a blood glucose reading of about 160 down to a projected blood glucose reading of 105 (an hour after the 160 reading).

In different implementations, the number of past readings that the processor considers to predict a future blood glucose reading can vary from implementation to implementation. However, in general, the readings used will typically start with the most recent glucose reading and usually span over a time period of between 5 minutes and 3 hours in the past.

The projected glucose reading may be calculated by evaluating the trend or slope in log-space. That is, instead of using the actual glucose values in the calculation above, the logarithms of the glucose values are used to calculate the slope or trend in values. Projecting out the logarithms of the glucose values will give a logarithm of the projectedBG. This can be turned into a projectedBG by exponentiating the logarithm of the projectedBG.

For example, to calculate the projectedBG in log-space for the illustrated example, one may take the natural logarithm (or any other base logarithm) of all of the values in the graph in FIG. 7. One may calculate the recent slope of the logarithm BGs and project out the logarithm of the BG by extending the slope to the logarithm of 160 (in the case of the natural logarithm, this value would be approximately 5.0751738), the current blood glucose level. In this example, this results in a logarithm of the projectedBG which can be used in the formula e (logProjectedBG) to obtain the actual projectedBG.

In some implementations, after the processor 202 determines a projected future blood glucose reading, it determines whether that projected future blood glucose reading is acceptable or not. In general, if the projected future blood glucose reading is acceptable, then the system 100 may continue to deliver insulin to the user according to the non-discretionary insulin delivery schedule.

In some implementations, the system 100 stores the range of acceptable readings for projected future blood glucose in memory 206. In those implementations, the processor 202 may determine if the projected future blood glucose reading is within the acceptable range by comparing the projected, future blood glucose reading with the range of acceptable readings stored in memory 206.

Even more particularly, in some implementations, the processor 202 calculates an error of the projected blood glucose reading relative to a range of acceptable blood glucose readings (stored, e.g., in memory 206). In that case, the error associated with a projected actual blood glucose level (projectedBG) can be a function of the projectedBG less an upper target of the target range, if the projectedBG is greater than the upper value; the error can be a function of the projectedBG less a lower target of the target range, if the projectedBG is less than the lower target; and the error would be zero if the projectedBG is greater than or equal to the lower target and less than or equal to the upper target.

In some implementations, the error calculated in this manner may be used to determine what, if any, the discretionary delivery should be. For example, if the magnitude of the error is zero (or at least below some threshold value) then the system 100 may exercise its discretion and decide to continue delivering insulin in an amount equal to what the non-discretionary delivery schedule would have called for as if a trigger had never occurred. If the magnitude of the error is non-zero (or above the threshold value) then, in certain implementations, the system 100 may use the calculated error to determine what, if anything, the discretionary insulin delivery should be.

In some implementations, the error may be computed as a function of the logarithm of the target and predicted glucose values. In such an implementation, the difference between the logarithm of the projectedBG and the logarithm of the relevant threshold target level (e.g., log (projectedBG)–log (target_threshold)) can be used to calculate the error.

The essence of the error used to calculate the dosing adjustment is that the error increases as the difference between the projectedBG value and the target range increases and the error decreases as the difference between the projectedBG value and the target range decreases. Note that the absolute value of the error should increase as the projectedBG moves away from the target range in either direction; the sign of the error is negative when the projectedBG is less than the target range and its sign is positive when the projectedBG is greater than the target range. Virtually any function that meets these criteria can be used to implement various implementations of the present disclosure.

Some implementations will create an adjusted-error based on some weighted sum of the errors over a previous period of time. This period of time may be virtually of any length. To calculate the adjustment to the error, the past may be broken into a discreet set of sub-periods, each with a corresponding error that was calculated at the time. Each sub-period may have a weighting associated with it; this weighting may be simple, such as equal weighting, where the weighting is equal to 1 for every sub-period.

In some implementations, the weighting may be a more complex function such as an exponential decay function where the sub-period weighting is assigned a value equal to e^(–alpha*period) where period is the number of sub-periods back from the current time and alpha is some positive real number. For example, if the sub-periods are five-minutes long, then a value for alpha of 0.03 would be a reasonable value in some embodiments. Other implementations may use arbitrary weighting schemes that may relate to the absorption profile of the insulin or virtually any function that is appropriate for the specific implementation.

Further, in some implementations, the periods used for calculating the adjustment to the error may be limited to the sub-periods that are between the current time and the most recent period where the glucose values cross some threshold level or levels (e.g., the top and bottom thresholds of a target glucose range.) For example, if the current glucose is 180 mg/dL and the single threshold is 120 mg/dL, then, under these circumstances, the calculation of the adjustment to the error would only include sub-periods between the current time and the most recent period where the glucose value was below 120 mg/dL. If the current glucose were 75 mg/dL, under the same circumstances, then the calculation would only include sub-periods between the current time and the most recent period where the glucose value was above 120 mg/dL.

In implementations that use the adjusted-error, the adjusted-error used for discretionary dosing decisions may be computed by summing the current instantaneous error of the system and the adjustment to the error as described above.

There are a variety of other ways that the processor 202 may (in implementing the discretionary delivery at 310) determine how much or when to deliver a discretionary dose of insulin. In some embodiments, the parameters of the discretionary delivery will always be within the boundaries of whatever the person has authorized. Additionally, under certain circumstances, the parameters may be constrained by other restrictions (e.g., restrictions related to safety, such as that a particular minimum amount of insulin must be delivered within a particular length of time, that a rate of insulin delivery must not exceed some specified maximum rate, etc.).

Figure 6:
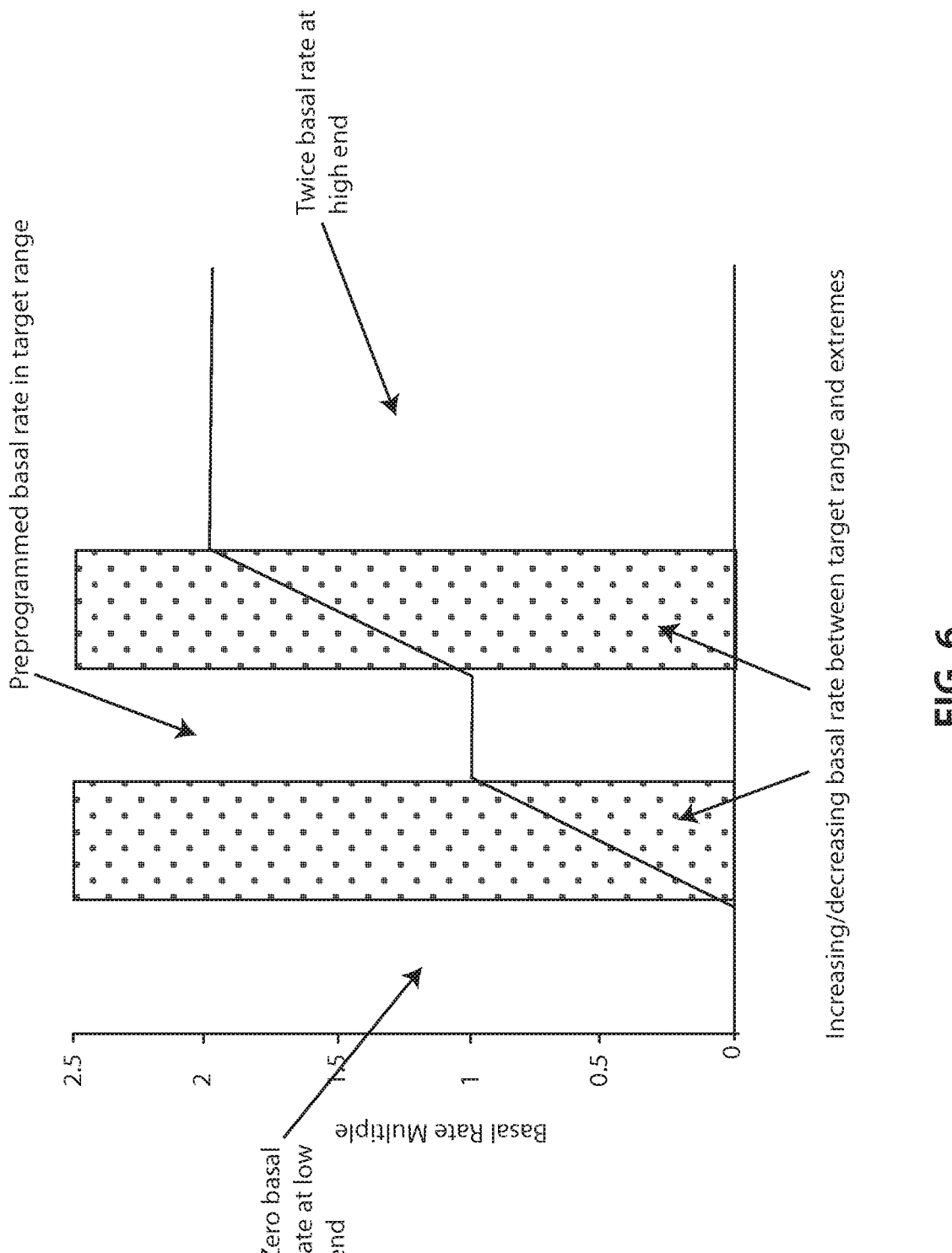
FIG. 6 is a plot of basal rate multipliers versus blood glucose levels.

In some instances, the parameters may be equal to the parameters entered by the person when he or she authorized the discretionary delivery. In some implementations, certain of the parameters may be constrained by one or more system constraints. In some instances, the parameters may call for a greater or lesser discretionary delivery depending, for example, on how far out of the bounds of the acceptable range a projected future blood glucose reading is. For example, in some implementations, the processor 202 multiplies the calculated error (between the projected future blood glucose reading and the range of acceptable readings) by some gain value and adds the result to the non-discretionary insulin delivery schedule to produce, in effect, a discretionary insulin delivery. An example of this is represented by the graph in FIG. 6. The gain value can be a constant value or it can be a function of the non-discretionary insulin delivery schedule such as a constant multiplied by the non-discretionary delivery rate for the current or future time.

In these instances, if a large adjustment is determined to be warranted, then the resulting discretionary delivery would reflect this; if, on the other hand, a small adjustment is determined to be warranted, then the discretionary delivery would reflect this.

There are a variety of other ways that the processor 202 can (as part of 310) determine how much discretionary insulin to deliver (i.e., make a dosing recommendation or identify parameters associated with a discretionary delivery). For example, in some implementations, the processor 202 can make a dosing recommendation based on the user's latest blood glucose reading.

Additionally, in some implementations, the processor 202 can make a dosing recommendation based on the user's latest blood glucose reading, a target blood glucose level that may have been specified by the person, and an estimated amount of insulin-on-board (IOB) for the user. Making a dosing recommendation based on these parameters, can include, for example, utilizing the following relationship:

$$\text{dose}\_t = \text{Max}(0,((BG\_cur - BG\_\text{target})/(C\_1*ISF)) - (C\_2*IOB) + C\_3),$$

where dose_t represents a recommended dosing at time t (a positive value or zero), BG_cur is the user's latest blood glucose reading, BG_target represents a target blood glucose level (or one or more outer boundaries of a range of acceptable blood glucose readings), ISF represents the user's insulin sensitivity factor and C_1, C_2, and C 3 are constants that may be used to tune the equation according to how aggressively the user wants to algorithm to run.

In a typical implementation, the insulin sensitivity factor reflects an amount that the user's blood glucose is lowered by the delivery of 1 unit of insulin. Insulin sensitivity can differ from user to user and within a user on a diurnal basis and/or from day to day.

Other possible ways that the processor 202 can make its dosing recommendation include: making the dosing recommendation based on an implied therapy using a fitting algorithm.

Making the dosing recommendation based on the implied therapy using the fitting algorithm can include, for example, utilizing the following relationship:

$$\text{dose}\_t = \text{Max}(0,(C\_1*(BGcur - BGtarg)/ISF) + (C\_2*COB/\text{carb\_ratio}) - (C\_3*IOB) + C\_4),$$

where dose_t represents a recommended dosing at time t (a positive value or zero), ISF represents the user's insulin sensitivity factor, COB represents carbohydrates-on-board for the user, carb_ratio represents the number of carbohydrates that one unit of insulin offsets for that individual and C_1, C_2, C_3 and C_4 are constants that may be used to tune the equation according to how aggressively the user wants to algorithm to run.

The phrase "carbohydrate-on-board," or COB, refers generally to an estimated amount of carbohydrates that the user has ingested into in his or her body but has not yet been absorbed. COB can be calculated based on a variety of factors, including the amount of carbohydrates recently ingested by the user, the time elapsed since those ingestions, a carbohydrate absorption function and one or more algorithms that estimate the remaining carbohydrates in the body based on one or more of the following: the historical glucose values, historical insulin dosing, and/or historical carbohydrate ingestion events.

The processor 202 also can make a dosing recommendation based on one or more of a target BG level, an IOB level, a carbohydrate-on-board (COB) level, or a rate or change of BG (or future predicted BG level), etc.

Predicting (or projecting) a future blood glucose reading can be accomplished utilizing one or more of the following approaches to extrapolate the future blood glucose reading: a proportional-derivative algorithm; a proportional, integral, derivative (PID) algorithm; an autoregressive forecasting model, such as autoregressive integrated moving average (ARIMA) models; or an algorithm based on physiological models of insulin and glucose transport.

Autoregressive integrated moving average (ARIMA) models may be parameterized on historical glucose data using techniques known to those skilled in the art (software such as MATLAB®, R, etc., provide functions to perform such a parameterization). In particular, an ARIMA (2,0,0) model also known as a second order autoregressive model, AR(2), does a reasonable job of modeling glucose levels. An AR(2) model may be used to create a projectedBG in lieu of a linear or log-linear forecast described earlier. An AR(2) model may fit the glucose data better by first log-transforming and mean-centering the data. This may be done by first taking the logarithm of the glucose data to create a time series of log-glucose values. Mean centering is then accomplished by subtracting the mean of all of the log-glucose values from each individual log-glucose value to create the time series on which the parameterization is performed.

AR(2) model forecasts may be created by iterating the AR equation BG_t=a1*BG_t−1+a2*BG_t−2+epsilon_t, where a1 and a2 are constants found in parameterizing the AR process and BG_t−x is the BG x time periods prior to the current time and epsilon_t is the error at any given point in time. To create the forecast, epsilons are set to zero and the initial BGs are set from the two most recent BG points. The process is repeated iteratively for each period forward by replacing the BG_t+x with the most recent projection and BG_t+x−1 with the second most recent projection. In the case of log-transformed and mean-centered AR parameterizations, the forecasts subsequently have the mean added back to the forecast values and this sum exponentiated to arrive at the actual glucose value forecasts.

Other algorithms for forecasting glucose levels include modeling the physiological systems of insulin and glucose transport. A number of compartmental models of glucose transport are known to those skilled in the art. These models may be used to forecast future glucose levels.

In essence, the processor 202 can implement any forecasting algorithm to predict (project) a future blood glucose reading. This projected glucose reading may then be used to calculate an error and adjust the discretionary insulin dosing.

Referring again to FIG. 3, according to the illustrated implementation, during the discretionary delivery, the processor 202 determines (at 312) if an alarm is warranted. In general, the alarm, which may be integrated into the controller 106 or the insulin pump 104, for example, may provide an indication to the person that any one or more of multiple different conditions has occurred. These conditions can include, for example, that the amount of insulin that has been delivered as the result of the system making the discretionary delivery (in 310) exceeds some threshold value. The threshold value in those implementations might be, for example, equal to all (or most) of the insulin that has been authorized for discretionary delivery to the user during the corresponding time period. In other implementations, the threshold value might be, for example, the fraction of sub-periods over a given time period where insulin was increased by a certain amount. The alarm may be a result of any one of multiple conditions that the user feels constitutes a condition that warrants an alarm due to a large amount of discretionary insulin delivery. This sort of alarm may be referred to as a high delivery alarm.

If the processor 202 determines (at 312) that there is no need to trigger an alarm and determines (at 314) that the discretionary delivery is complete, then the system 100 reverts to step 304 and delivers insulin to the user according to the non-discretionary insulin delivery schedule.

If the processor 202 (at 312) determines that the alarm should be triggered, the processor 202 (at 316) causes the alarm to be triggered. The alarm can be audio, visual, tactile or a combination thereof.

In some implementations, when triggered, the alarm provides an indication to the person as to the condition or conditions that caused the alarm to be triggered. This can be done in a variety of ways. For example, a message may appear on a user interface screen of the controller and/or pump indicating the cause of the alarm.

Moreover, in some implementations, the system 100 provides the person with the ability to acknowledge (and/or silence) the triggered alarm. This may be done in a variety of ways as well. For example, a touch sensitive "SILENCE ALARM" button may appear on the user interface screen of the controller 106 and/or pump 104 while the alarm is in a triggered state. Selection of the "SILENCE ALARM" button, in those instances, may cause the alarm to become silenced. In addition, in some implementations, the person's acknowledgement (or silencing) of the alarm may be considered a verification to the system 100 that the person considers the alarm condition (e.g., the high delivery that caused a high delivery alarm) to be an acceptable condition. In some implementations, one or more verification or confirmation actions, which are separate from the alarm silencing action, may be required to indicate to the system 100 that the person understands the alarm condition and considers it to be an acceptable condition.

In some implementations, the processor 202 is configured to determine (at 318) if the alarm has been acknowledged (e.g., silenced) by the person in a timely manner (e.g., 30 seconds, 1 minute, 2 minutes, etc.).

According to the illustrated implementation, if (at 318) the alarm is acknowledged (e.g., silenced) in a timely manner, then the system 100, according to the illustrated example, reverts to step 304 and delivers insulin to the user according to the non-discretionary delivery schedule.

In some implementations, if the alarm is acknowledged in a timely manner, the system 100 subsequently delivers insulin to the user according to a non-discretionary schedule of delivery, according to a new, discretionary delivery schedule that the person may subsequently be prompted to approve or enter or some combination of both non-discretionary and discretionary deliveries.

If the triggered alarm (at 316) is a high delivery alarm and the alarm is not acknowledged (at 318) in a timely manner (e.g., because the person is sleeping or otherwise unable to acknowledge the alarm), then, according to the illustrated implementation, the system 100 subsequently and automatically (i.e., without specific instructions from the person) delivers (at 320) less insulin to the user than would be delivered if the system 100 were operating according to the non-discretionary insulin delivery schedule.

In some implementations, subsequently delivering less insulin than would be delivered according to the non-discretionary schedule of delivery might include delivering an amount that is between 0 and a multiple of the first threshold amount less than what would be delivered according to the non-discretionary schedule of delivery over a certain period of time. This can prevent the excess insulin from incorrectly lowering blood glucose level or, in some cases, allow glucose levels to revert from the lower levels caused by unacknowledged additional discretionary dosing.

The first threshold amount can be, for example, a first predetermined amount of insulin above what would have been delivered to the user according to a non-discretionary delivery schedule over the specific time period, and the second threshold amount can be a second predetermined amount of insulin less than what would have been delivered to the user according to the non-discretionary delivery schedule over the specific time period.

There are a variety of ways that the system 100 (e.g., the processor 202) can determine how much the amount or rate of insulin will be reduced following an unacknowledged alarm. Typically, the reduction is such that it will, in a reasonable amount of time (e.g., within 1-3 hours) at least partially (or entirely) offset any extra insulin above the non-discretionary delivery the user may have received as a result of the discretionary delivery. The reduction can, in some implementations, be relative to whatever amount or rate would be called for by the non-discretionary delivery schedule.

If, at some point, while the system is implementing step 320, the reduction of insulin delivery relative to the non-discretionary delivery schedule is deemed (e.g., by the processor 202) at 322 to be sufficient to have offset enough of the maximum amount of authorized discretionary insulin that was delivered to the user (during 310), then the system 100 reverts to step 304 and delivers insulin to the user according to the non-discretionary delivery schedule. Otherwise, according to the illustrated implementation, the system 100 keeps delivering less insulin to the user than the non-discretionary delivery schedule would have called for.

In some implementations, the processor 202 (at 312) determines whether the alarm is warranted based on whether a cumulative amount of discretionary insulin delivered during a specific time period has either exceeded a first threshold amount or is below a second threshold amount. In some of those implementations, the system 100 may be configured to trigger the alarm (at 316) if either of these conditions exist.

In some implementations, the system 100 performs step 312 in FIG. 3 (i.e., determining whether an alarm is warranted) on an iterative basis. In this regard, the specific time period for which data is considered for each iteration may be some period of time prior to that iteration. For example, in one implementation, the system 100 may be adapted to perform step 312 every five minutes, based on a rolling four-hour window of data. In that example, the system 100 would make a new determination every five minutes as to whether an alarm is warranted based on four hours of data preceding when the new determination is being made. In the event of a termination of discretionary delivery due to a breach in this regard (i.e., a determination that an alarm is warranted), some implementations cease all iterative steps as well.

Figure 4:
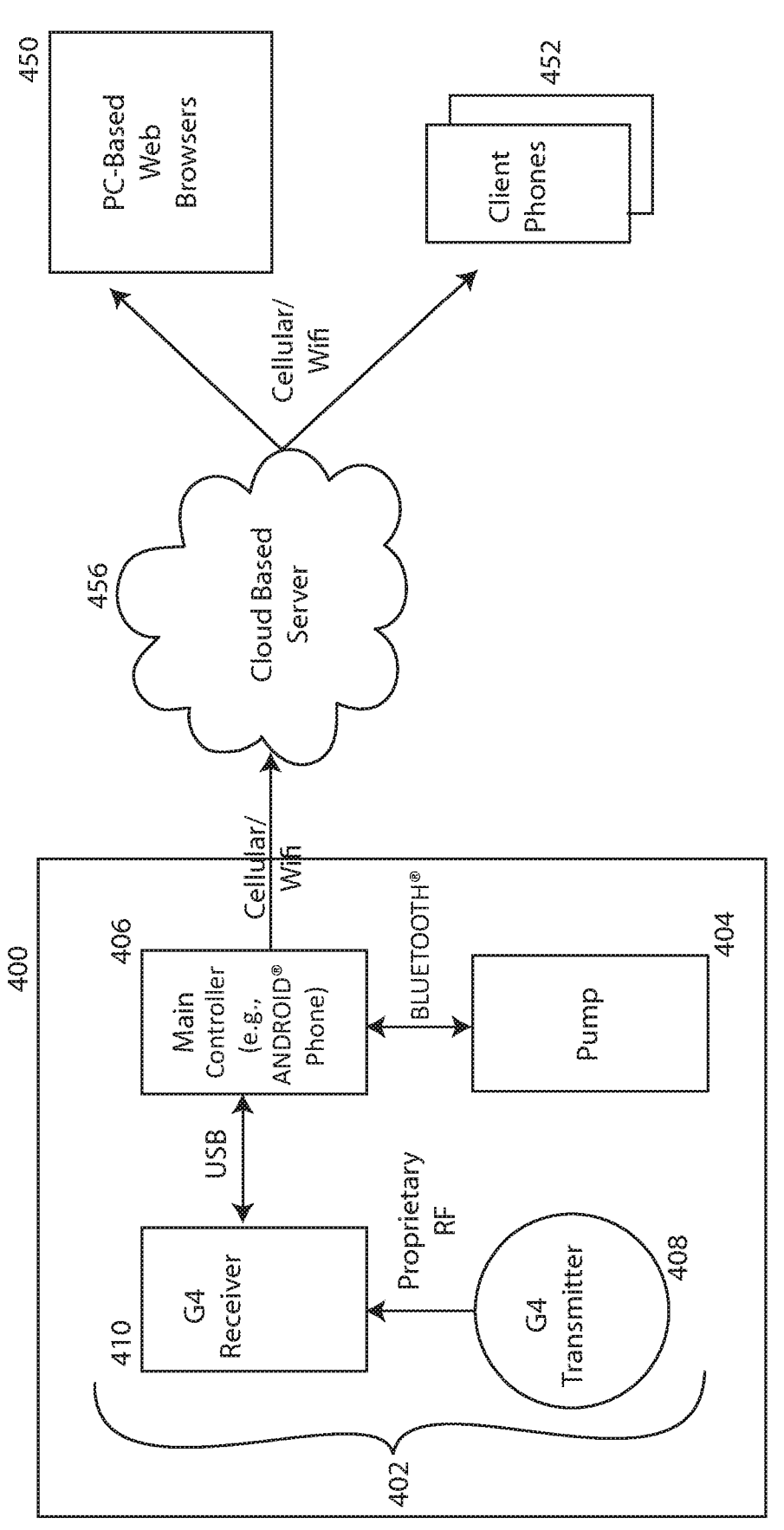
FIG. 4 is a schematic diagram of an exemplary system adapted to facilitate the functionalities disclosed herein for a particular user and to communicate or interact with one or more PC-based web browsers and client phones over a wireless network.

FIG. 4 is a schematic diagram of an exemplary system 400 adapted to facilitate the functionalities disclosed herein for a particular user, and to communicate or interact with one or more PC-based web browsers 450 and client phones 452 over a wireless network (having, e.g., a cloud-based server 456).

In some implementations, the exemplary system 400 in FIG. 4 has a similar structure and similar functionalities as the system 100 shown in FIG. 1. In exemplary system 400, a glucose monitoring device 402 includes a sensor unit 408 that attaches to the user, such as by adhering to the skin of the user, and a handheld CGM controller unit 410. In this implementation, sensor unit 408 has a transmitter that utilizes proprietary radio frequency (RF) technology to communicate with the CGM controller unit 410. The CGM controller unit 410 may include a processor for receiving sensor data from sensor unit 408 and converting the sensor data into corresponding blood glucose values. In some implementations, CGM controller unit 410 includes additional functionality, such as features that allow the glucose monitoring device 402 to be calibrated, and a display screen to indicate blood glucose values and/or trends to the user. The CGM controller unit 410 in turn communicates with controller 406, such as a smartphone. This communication may be accomplished with a USB cable as shown, or through a transmitter or transceiver in CGM controller unit 410 that communicates with a corresponding receiver or transceiver at the controller 406. In addition, the pump in this implementation uses BLUETOOTH® RF to communicate with the controller 406. The system 400 communicates to the cloud-based server 456 and the cloud-based server 456 communicates with the PC-based web browsers 450 and the client phones 452 using cellular or Wi-Fi technology.

The specific communication technologies that the various system components utilize can vary considerably. Additionally, the function of each component shown in FIG. 4 may instead be performed by multiple components, or two or more components shown may be combined. For example, in some implementations (not shown), the functionality of the CGM controller unit 410, the controller 406, and the pump 404 may be combined in a single pump unit, such that the CGM sensor unit 408 and the cloud-based server 456 communicate directly with the single pump unit. In some implementations, the sensor unit 408 may be combined with the infusion set (not shown) that delivers insulin from the pump to the user through the user's skin.

Other implementations may or may not include any cloud-based components. In some implementations, a cloud-based server 456 transmits blood glucose values, trends, histories, alarm conditions, non-discretionary and/or discretionary settings, and/or other information from local system 400 to the cloud-based server 456, web browsers 450, and/or mobile devices 452. In some embodiments, information, settings, control commands and/or other information may be transmitted from the web browsers 450 and/or mobile devices 452 to the cloud-based server 456 and/or local system 400. In some embodiments, some or all of these cloud-based communications may be encrypted, limited with other security measures, or not provided at all in order to reduce risk of inadvertent or intentional dosing problems, for example.

Figure 8:
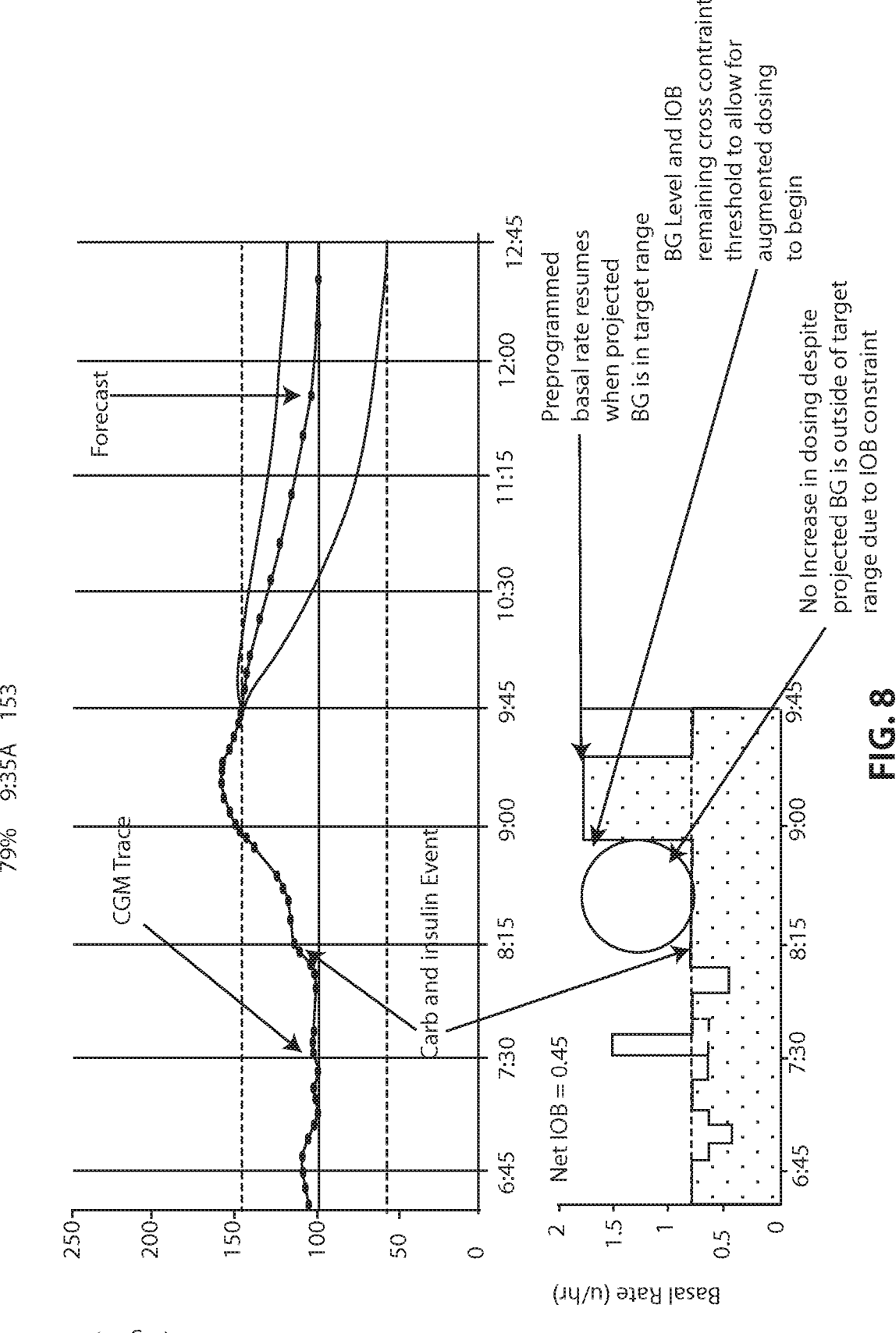
FIG. 8 is an exemplary representation of the behavior of the system in FIG. 1.

Referring to FIG. 8, the illustration shows the operation of an exemplary system that allows for adjusting basal rates between zero and twice the non-discretionary, pre-programmed basal rate. In other implementations, the minimum basal rate is greater than zero and/or the maximum allowed basal rate is more or less than 200% of the non-discretionary, pre-programmed basal rate. This exemplary system provides for discretionary delivery of basal insulin in lieu of the non-discretionary, pre-programmed basal rate.

The entire period depicted in the figure shows the system in a discretionary delivery mode. The upper portion shows an example of a user's blood glucose levels plotted against a time axis, and the lower portion shows an associated insulin delivery rate (represented by the shaded areas) to the user also plotted against the same time axis. The solid line in the lower figure represents the basal rate that the system desires to have set at any point in time, and the top edge of the shaded region represents the basal rate that was actually delivered. During various periods (for example, 7:35-7:50) the solid line deviates from the top edge of the shaded region (a dashed line in this time period) because the controller 106 is unable to change the basal rate on the insulin delivery device 104 due to communication errors in the system 100 (or 400). The dotted line at 0.8 U/hour on the lower portion indicates the pre-programmed, non-discretionary basal rate. The insulin delivery represented in the illustrated graph represents how the system 100 in FIG. 1, for example, might deliver insulin to the user.

The blood glucose levels up until 9:45 a.m. represent actual blood glucose readings (e.g., from a glucose monitoring device, such as 102 in FIG. 1), whereas the blood glucose levels after 9:45 a.m. represent future blood glucose level predictions.

According to the illustrated time plot, up until about 8:15 a.m., the delivery of insulin is largely responsive to the changes in the user's blood glucose readings. As can be seen, slight variations in the slope of the recent glucose values cause minor decreases in the discretionary basal rate delivery during this period. A glucose value increase at 7:35 warranted an increase in basal rate delivery by the system; however, a communication problem precluded the system from increasing the rate. Subsequently, at 7:50, the rate reverted to the non-discretionary basal rate since the glucose level and rate of change indicated an in-target predicted glucose level.

At about 8:15, there is an increase in the user's blood glucose reading that might, under certain circumstances, suggest that an increase in the delivery rate of insulin might be appropriate. This increase in blood glucose reading may be a response to the user ingesting carbohydrates, for example. More particularly, at 8:15, in the illustrated example, the recent upward trend in blood glucose readings suggests that, in the future, the user's blood glucose level will be unacceptably high.

However, as can be seen, there is no increase in the rate of insulin delivery at 8:15 despite the fact that the recent upward trend in blood glucose readings suggests that, in the future, the user's blood glucose level will be unacceptably high. This is because, in the illustrated example, the system 100 is constrained from increasing the insulin delivery rate by the user's IOB (insulin-on-board), for example by using the IOB constraints described herein. In essence, the system 100 does not increase the insulin delivery rate, even though the blood glucose readings show an upward trend, because the user's IOB suggests that the insulin already in the user's body may be sufficient to effectively manage the recent upward trend in user's blood glucose readings. The period of time during which the IOB constraint is in effect is represented by the circle in the lower part of the time graph.

According to the illustrated example, the user's blood glucose readings continue to increase while the system 100 is constrained from increasing the insulin delivery rate by the user's IOB.

Just before 9:00 a.m., the system 100 increases the insulin delivery rate. This increase is in response to the continuing upward trend in blood glucose readings and the user's IOB remaining. In essence, just before 9:00 a.m. in the illustrated example, the user's blood glucose readings and IOB remaining cross the IOB constraint threshold (as described in FIG. 5) to allow the system 100 to allow augmented dosing to begin.

Throughout the discretionary delivery, the exemplary system may iteratively perform alarm constraint checks, for example, to see if the net amount of discretionary insulin dosed over the past 3 hours is greater than 1.5 units. In some implementations, this check is done every 5 minutes. If the system determines (not shown) that the net amount of discretionary insulin delivery over the past 3 hours is greater than the allowed amount of 1.5 units, the system is configured in some implementations to take actions to alert and potentially reverse any excess insulin delivered as described in steps 316, 318, and 320 herein, shown in FIG. 3.

Referring back to FIG. 8, shortly after the augmented dosing begins, the user's blood glucose readings hit a local maximum and begin coming down. Once the projected future blood glucose readings are within an acceptable target range (at about 9:25 a.m.), the system 100 reverts the discretionary delivery to a level equal to the non-discretionary basal rate. In this exemplary system, the discretionary delivery will continue into the future until the user manually terminates the discretionary delivery or a user constraint (such as a maximum or minimum dosing constraint) is breached.

Figure 9:
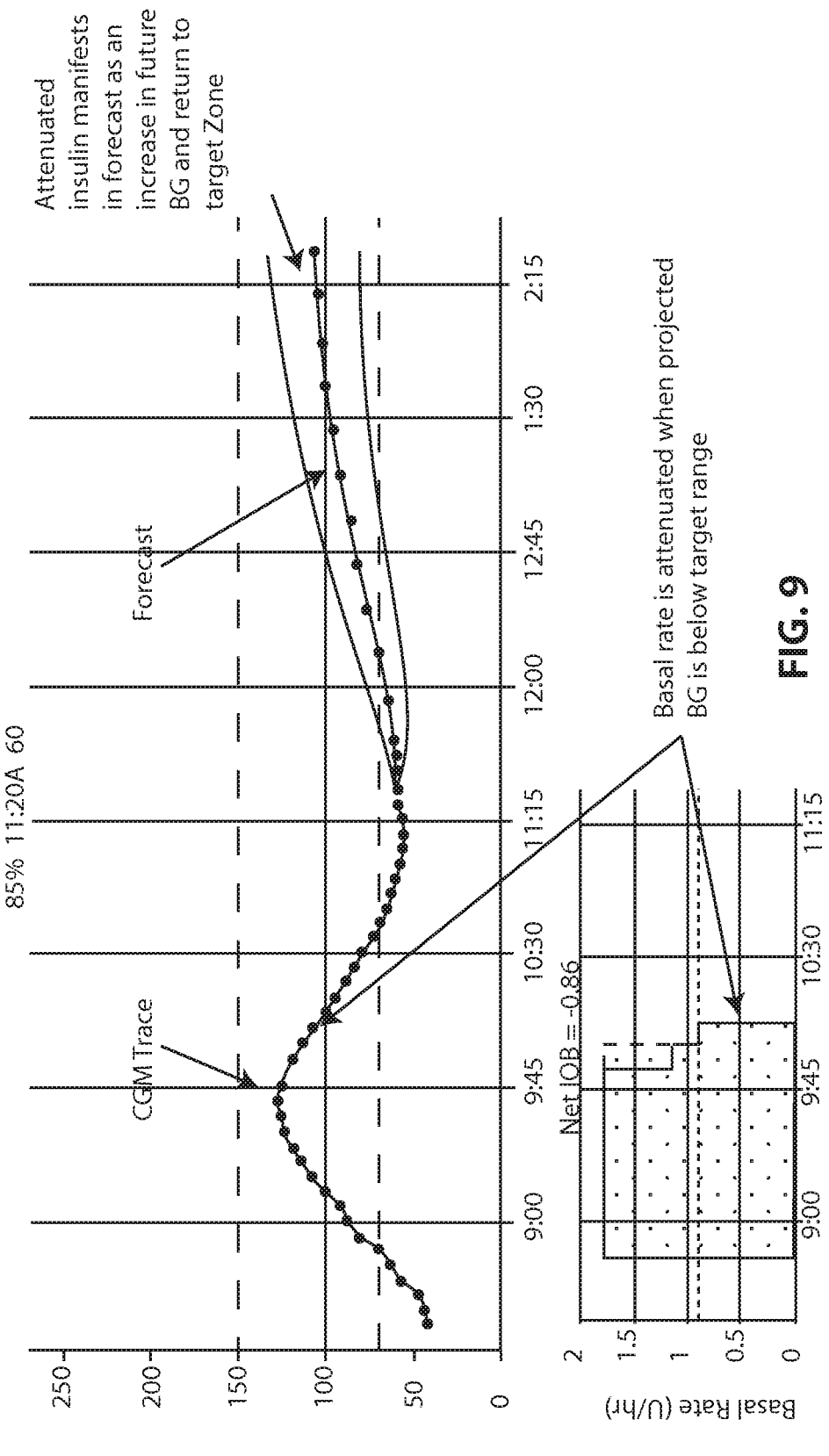
FIG. 9 is another exemplary representation of the behavior of the system in FIG. 1.

FIG. 9 provides another illustrated example of the operation of an exemplary system that allows for adjusting basal rates between zero and twice the non-discretionary, pre-programmed basal rate in lieu of the non-discretionary, pre-programmed basal rate. As in FIG. 8, the entire period shown is in discretionary delivery mode. The upper portion shows an example of a user's blood glucose levels plotted against a time axis, and the lower portion shows an associated insulin delivery rate (represented by the shaded areas) to the user also plotted against the same time axis. The solid line in the lower figure represents the basal rate that the system desires to have set, and the top edge of the shaded region represents the basal rate that was actually delivered. During various periods (for example, 9:50-9:55), the solid line deviates from the top edge of the shaded region (a dashed line in this time period) because the controller 106 is unable to change the basal rate on the insulin delivery device 104 due to communication errors in the system 100 (or 400). The dotted line at 0.8 U/hour on the lower portion indicates the pre-programmed, non-discretionary basal rate. The insulin delivery represented in the illustrated graph represents how the system 100 in FIG. 1, for example, might deliver insulin to the user.

According to the illustrated plot, the insulin delivery is attenuated to zero from 8:30 to 8:50 due to the low glucose level and no indication from the rate of change of glucose level that it will increase sufficiently.

At 8:55, a marked increase in the glucose level causes the system to increase the basal rate to 1.6 U/hour—twice the non-discretionary basal rate—in an attempt to avert a glucose level above the desired range. This increase is held until the glucose values crest around 9:45 in the target range.

At this point the system attempts to revert the basal rate (at first unsuccessfully at 9:50, then with success at 9:55) to a level close to the non-discretionary basal rate of 0.8 U/hour. This level is short-lived, however, as the decrease in the level and slope of the glucose values at 10:00 and beyond cause the system to lower the discretionary delivery rate to 0 U/hour.

The rate of 0 U/hour will remain set until, at some future point (not shown), the projected BG of the system indicates a level closer to the target range or, in some implementations, until a low dosing insulin alarm is triggered. A low dosing alarm occurs when the amount of insulin delivered during a window of a discretionary delivery period is less than a predetermined threshold value.

Figure 10:
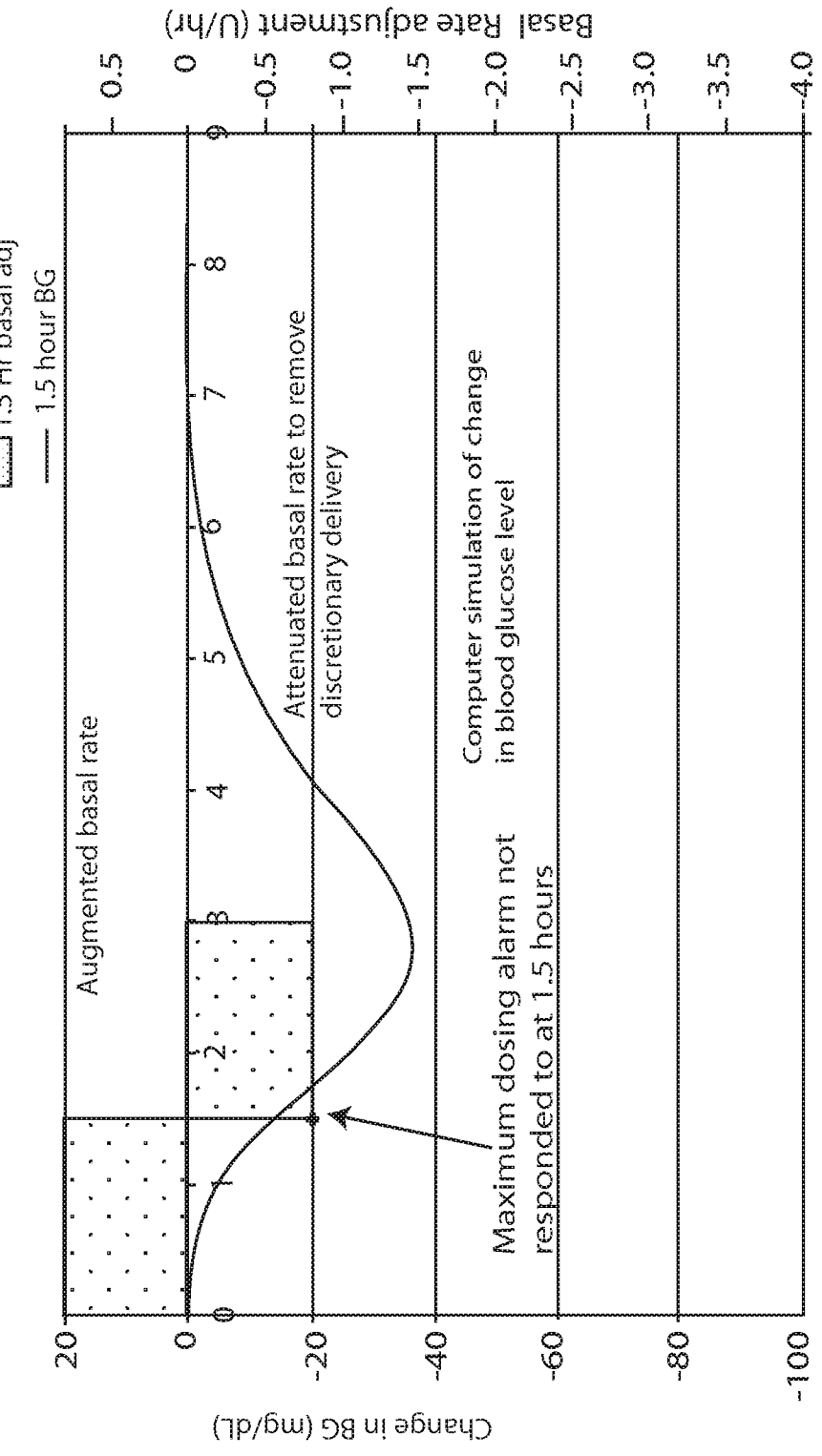
FIG. 10 is a time plot showing a computer simulation of the effect on glucose level after a maximum discretionary limit alarm has been triggered but remains unacknowledged.

FIG. 10 provides an illustrated example of the benefit of the high delivery alarm safety mitigation described herein at step 320 (as shown in FIG. 3). The figure shows a computer simulation of a high delivery alarm 318 that is unacknowledged and where the system 100 subsequently attenuates the delivery of the insulin at 320. In the illustrated example, the system is providing discretionary delivery in lieu of the pre-programmed, non-discretionary basal rate. The shaded areas show the time varying adjustment to the non-discretionary basal rate as indicated by the right y-axis in hours from the start of the simulation. In this illustrated example, the non-discretionary basal rate is set to 0.8 U/hour. Thus, the adjustment of 0.8 U/hour from time 0 to time 1.5 hours reflects an actual basal rate of 1.6 U/hour. Additionally, the adjustment of −0.8 U/hour from time 1.5 hours to time 3 hours reflects an actual basal rate of 0 U/hour.

The solid line shows a time varying plot of the computer-simulated change in glucose level, as indicated by the left y-axis in hours from the start of simulation. In this exemplary system, the maximum discretionary insulin delivery amount is set to the insulin that would be delivered in 1.5 hours of pre-programmed, non-discretionary basal rate delivery which equals, in this case, 1.2 units of insulin. As noted, a high delivery alarm is set off at 1.5 hours when the maximum discretionary delivery amount is reached. In the illustrated example, the alarm remains unacknowledged, causing the system to enter into a removal of the augmented delivery as described in step 320.

By delivering less than the pre-programmed, non-discretionary basal rate, the system is effectively removing insulin from the delivery profile. Because, as a part of the normal course of insulin replacement therapy, the user needs the pre-programmed basal insulin delivery to maintain a static glucose level, the effect of delivering less than the pre-programmed insulin rate results in a rise in the user's glucose level. The difference between the pre-programmed basal delivery and the actual insulin delivery is effectively insulin that is "removed" from the user with the expected rise in glucose values equal to the absolute value of the expected decline that the removed amount of insulin would reduce the user's glucose levels.

Referring back to FIG. 10, after the alarm is triggered the glucose level continues to drop for about an hour after which it levels off and then begins to increase reflecting the effect of the removed insulin. At the end of the simulation, the glucose level has reverted to the original level before any adjustments to the system had been made.

As can be seen from this example, the subsequent removal of discretionary delivery upon an unacknowledged maximum dosing alarm provides a robust safety mitigation to a possible unintended over-delivery of insulin by a discretionary delivery system. The benefits for a user of such a system are obvious including mitigation of potentially extended, unintended, and possibly severe hypoglycemia.

Figure 11:
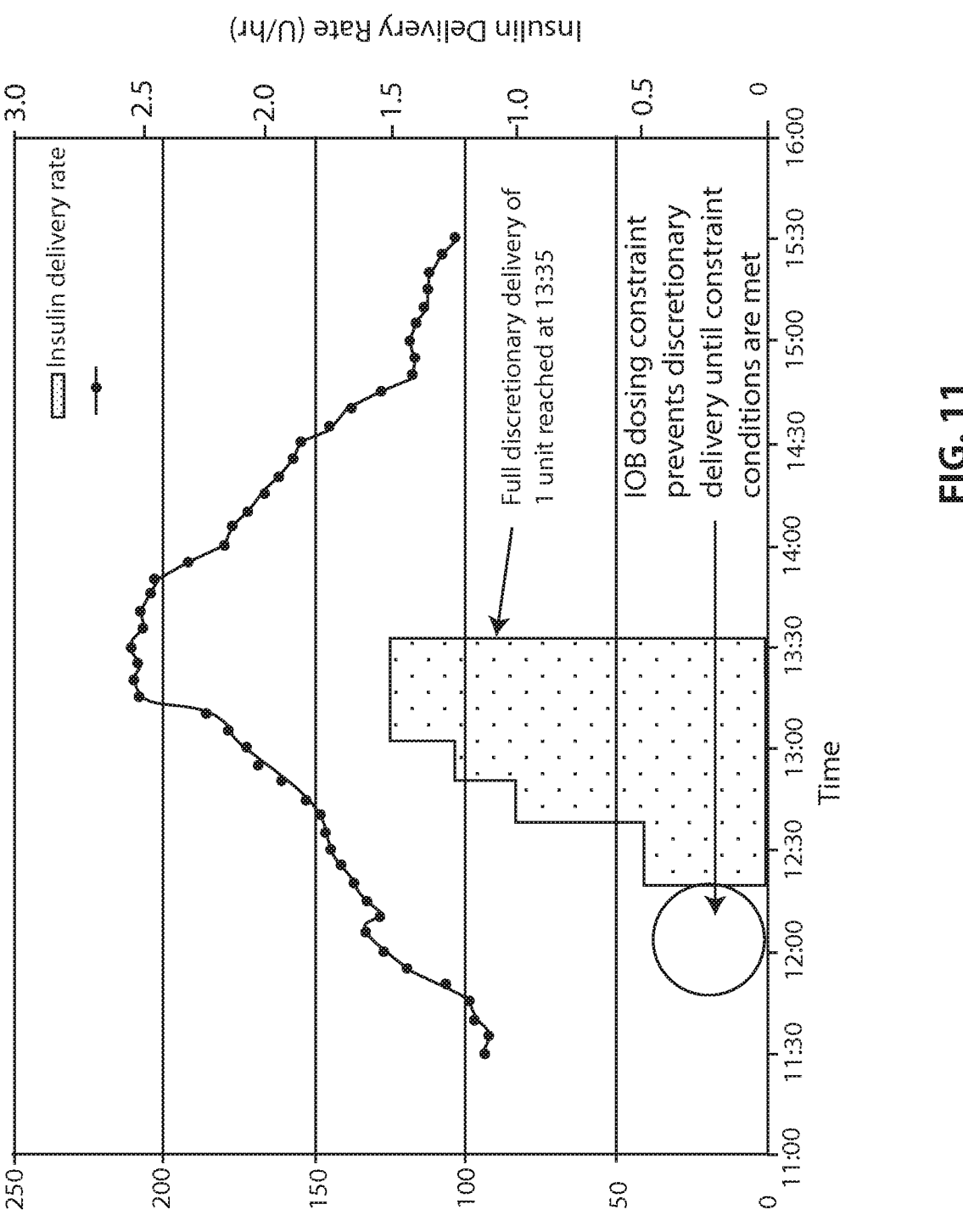
FIG. 11 is an exemplary representation of the behavior of the system in FIG. 1.

Referring to FIG. 11, another exemplary system is shown that doses insulin in addition to a non-discretionary basal rate. This exemplary system allows for constrained discretionary boluses; the discretionary boluses in the system allow for a maximum rate of delivery, maximum amount and maximum time to deliver the insulin. In some implementations, the discretionary bolus includes an IOB constraint.

The illustrated example shows how, in one implementation, the system may use its discretion to deliver a 1 unit discretionary bolus. In the figure, the dotted line plotted on the left y-axis is the glucose level of the user. The solid shaded area on the bottom of the graph reflects discretionary insulin delivery rates over time as defined by the right y-axis. This discretionary insulin delivery is in addition to the non-discretionary, pre-programmed basal rate that the system continues to deliver throughout the discretionary bolus delivery.

Referring to FIG. 11, a meal occurs at or around 11:30 that includes the ingestion of carbohydrates and the need to dose insulin to offset them. In the illustrated example, the user doses a non-discretionary bolus of 3 units to cover the insulin requirements of the majority of the meal and additionally doses a discretionary bolus of 1 unit to be delivered over at most 3 hours with a delivery rate not to exceed 1.5 U/hour or 150% of the user's pre-programmed, non-discretionary basal rate of 1 U/hour. The user sets this discretionary bolus to include an IOB constraint such that discretionary insulin will only be delivered if the user constraint of IOB vs glucose level is met.

In some situations, a user may desire to bolus for their meal in this way if, for example, the user is uncertain as to how much insulin will be required for the meal. In this case, the user may bolus for the minimum amount of insulin he or she is confident will be needed and then use a discretionary bolus for the amount that may or may not be additionally needed. In this illustrated example, the non-discretionary bolus is 3 units and the discretionary bolus delivery is between 0 and a maximum of 1 unit with the constraints detailed above.

Referring back to FIG. 11, the user's glucose level starts to increase around 11:45 due to the ingestion of the meal. From 11:45 to 12:20, the glucose trend indicates that the system should, in some implementations, deliver some of the discretionary insulin bolus, however, due to the IOB constraint the discretionary delivery is not made during this period. The period where the IOB constraint is in effect is shown by a circle in the diagram.

At 12:20, the IOB constraint is breached and the system begins to deliver the discretionary bolus. The infusion rate at which the bolus is delivered increases as the glucose level and slope of the glucose level increase until the delivery rate hits the maximum allowable delivery rate of 1.5 U/hour at 13:05. Despite the system desiring to increase the delivery rate higher than 1.5 U/hour, the maximum delivery rate constraint prevents it from doing so.

At 13:35 the cumulative sum of the discretionary insulin delivery reaches the maximum allocated amount of 1 unit. After this occurs, the discretionary delivery mode ceases and the system reverts back to non-discretionary mode where it continues to dose the pre-programmed basal rate and other non-discretionary requests that are made by the user.

Figure 12:
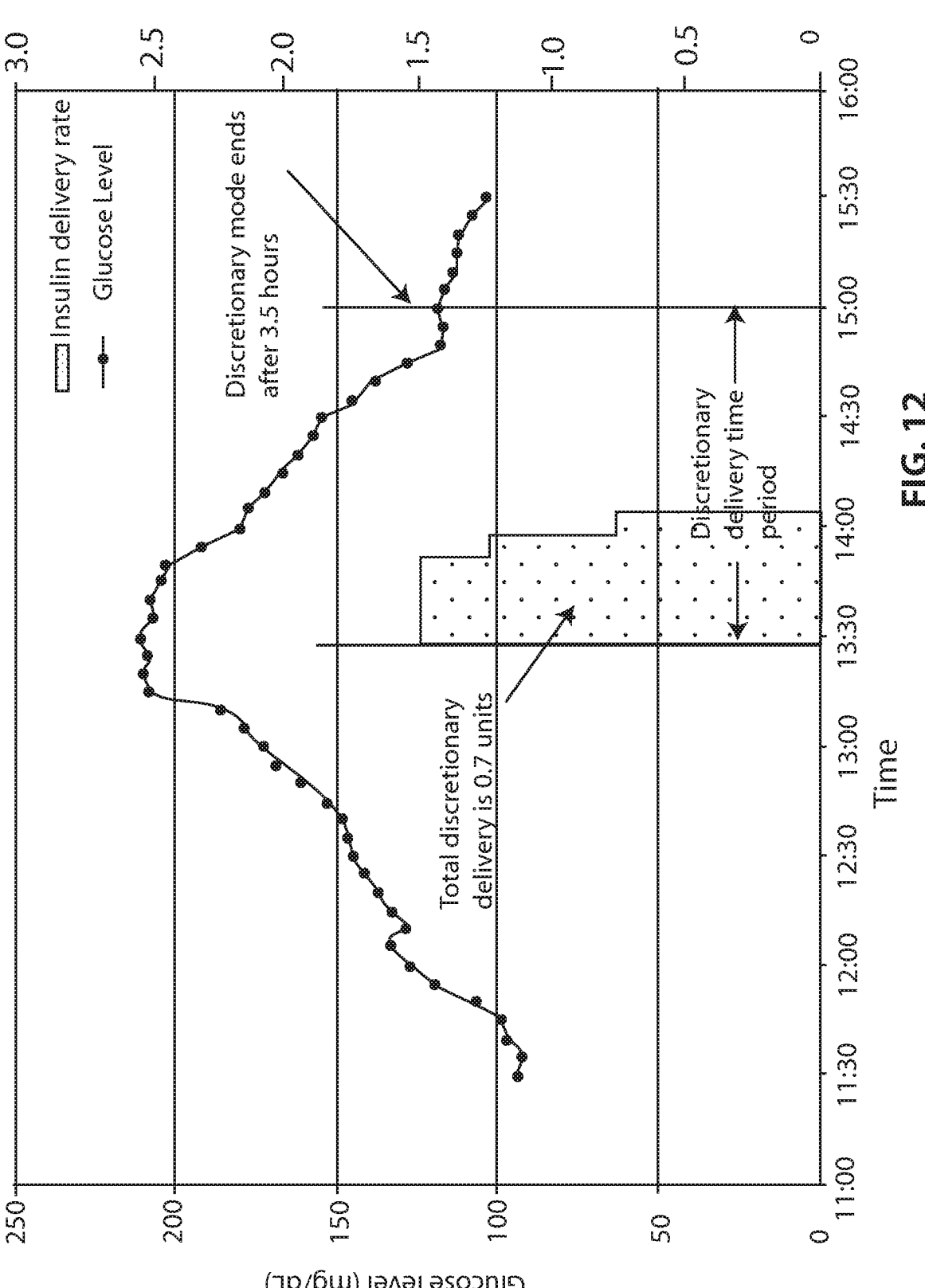
FIG. 12 is an exemplary representation of the behavior of the system in FIG. 1.

FIG. 12 illustrates another exemplary system that doses discretionary insulin in addition to a non-discretionary basal rate. Similar to the system in FIG. 11, this exemplary system allows for constrained discretionary boluses; the system allows for a maximum rate of delivery, maximum amount of insulin and maximum time to deliver the insulin. In some implementations, the system allows for an additional time constraint for the earliest that the discretionary delivery can occur.

The illustrated example shows how, in some implementations, the system may use its discretion to deliver a 1 unit discretionary bolus. In the figure, the solid line plotted on the left y-axis is the glucose level of the user. The solid shaded area on the bottom of the graph reflects discretionary insulin delivery rates over time as defined by the right y-axis. This discretionary insulin delivery is in addition to the non-discretionary, pre-programmed basal rate that the system delivers.

Referring to FIG. 12, a meal occurs at or around 11:30. The user doses a non-discretionary bolus to cover the insulin requirements of the majority of the meal and additionally doses a discretionary bolus of 1 unit to be delivered only between 2 and 3.5 hours later with a delivery rate not to exceed 1.5 U/hour or 150% of the user's pre-programmed, non-discretionary basal rate of 1 U/hour.

In this exemplary situation, the user may choose to delay the start of the discretionary delivery due to the composition of the meal he or she is consuming. High fat meals such as pizza may have delayed absorption potentially requiring insulin significantly later than when the meal occurs. In this illustrated example, the user chooses to give a discretionary bolus 2 hours in the future, when, for example, the user may see an increase in glucose levels as a result of this delayed absorption.

Referring again to FIG. 12, we see that no discretionary insulin is delivered prior to 13:30 despite elevated glucose levels per the 2 hour minimum delay constraint. At 13:30, the system implements a discretionary delivery of 1.5 U/hour, the maximum allowed by the constraints of the discretionary bolus due to the high level of projected glucose. As the glucose levels decline around 14:00, the discretionary delivery rate decreases until the system ceases discretionary delivery at 14:05. The system does not dose any more insulin throughout the remainder of the discretionary delivery period.

The total insulin delivered for this discretionary bolus is 0.7 units which is less than the maximum amount allowed of 1 unit. At 15:00, the discretionary delivery period ends and the system continues forward by dosing the pre-programmed basal rate and other non-discretionary requests that are made by the user.

A number of embodiments of the present disclosure have been described. Nevertheless, it will be understood that various modifications may be made without departing from the spirit and scope of the disclosure.

For example, this specification contains many specific implementation details. However, these should not be construed as limitations on the scope of any inventions or of what may be claimed, but rather as descriptions of features specific to particular embodiments of the present disclosure. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Processors suitable for the execution of a computer program include, by way of example, both general- and special-purpose microprocessor structures, and any one or more processors of any kind of digital computer. Generally, a processor will receive instructions and data from a read-only memory or a random access memory or both. The elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical discs, or optical discs. However, a computer need not have such devices. Moreover, a computer can be embedded in another device, e.g., an insulin pump, an electronic pump controller, a continuous glucose monitor, a mobile telephone or a personal digital assistant (PDA), to name just a few.

Devices suitable for storing computer program instructions and data include all forms of non-volatile memory, media and memory devices, including, by way of example, semiconductor memory devices, e.g., EPROM, EEPROM, and Flash memory devices; magnetic discs, e.g., internal hard disks or removable disks; magneto-optical discs; and CD-ROM and DVD-ROM discs. The processor and the memory can be supplemented by, or incorporated in, special-purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser. Thus, a user interface of the inventive systems and methods described herein may be remote from a computer-based processor of the system, and may be operated by a user and/or a caregiver.

Aspects of the disclosure can take the form of an entirely hardware embodiment, an entirely software embodiment or an embodiment containing both hardware and software elements. In some embodiments, aspects of the disclosure are implemented in software, which includes, but is not limited to, firmware, resident software, microcode, etc. Furthermore, the aspects of the disclosure can take the form of a computer program product accessible from a computer-usable or computer-readable medium providing program code for use by or in connection with a computer or any instruction execution system. For the purposes of this description, a computer-usable or computer-readable medium can be any tangible apparatus that can contain, store, communicate, propagate, or transport the program for use by or in connection with the instruction execution system, apparatus, or device.

As used herein, a computer-readable medium or computer-readable storage medium, or the like, is intended to include hardware (e.g., registers, random access memory (RAM), non-volatile (NV) storage, to name a few), but may or may not be limited to hardware. The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random access memory (RAM), a read-only memory (ROM), a rigid magnetic disk and an optical disc. Current examples of optical disks include compact disc-read-only memory (CD-ROM), compact disc-read/write (CD-R/W). Some portions of the detailed description may be presented in terms of algorithms and symbolic representations of operations on data or data bits that may be, for example, within a computer memory. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that these and similar terms are to be associated with the appropriate physical quantities and are merely convenient labels applied to these quantities. Unless specifically stated otherwise or as apparent from context, it is appreciated that throughout the description, discussions utilizing terms such as "processing" or "computing" or "calculating" or "determining" or "displaying" or the like, refer to the action and processes of a computer system, or similar electronic computing device, computer-based processor, etc., that manipulates and transforms data represented as physical (electronic) quantities within the computer system's registers and memories into other data similarly represented as physical quantities within the computer system memories or registers or other such information storage, transmission or display devices.

Other embodiments are within the scope of the appended claims.

What is claimed is:

1. A method, comprising:

receiving a user input defining a set of parameters of a discretionary insulin delivery mode of a system configured to deliver insulin to a user, wherein, when the system operates within the discretionary insulin delivery mode, the system, without further input from the user, is permitted to deliver discretionary insulin to the user according to a variable basal rate between an upper threshold basal rate and a lower threshold basal rate responsive to events associated with the user and within the defined set of parameters;

responsive to receiving an indication of an event associated with the user:

determining, via the system, the lower threshold basal rate to comprise a first basal rate that is lower than a constant basal rate of a non-discretionary insulin delivery that would have been delivered to the user according to a non-discretionary insulin delivery schedule absent receiving the indication of the event;

determining, via the system, the upper threshold basal rate to comprise a second basal rate that comprises the constant basal rate of the non-discretionary insulin delivery that would have been delivered to the user according to the non-discretionary insulin delivery schedule absent receiving the indication of the event in addition to a basal rate determined based on the indication of the event; and starting the discretionary insulin delivery mode of the system and delivering an amount of the discretionary insulin to the user according to the variable basal rate; and responsive to tracked discretionary insulin delivered to the user and a received glucose value, ceasing the discretionary insulin delivery mode of the system and delivering an amount of non-discretionary insulin to the user according to the non-discretionary insulin delivery schedule having the constant basal rate, wherein the system is not permitted to adjust the non-discretionary insulin delivery within the non-discretionary insulin delivery schedule.

2. The method of claim 1, wherein delivering the discretionary insulin to the user comprises delivering the discretionary insulin in addition to the non-discretionary insulin delivered according to the non-discretionary insulin delivery schedule.

3. The method of claim 1, wherein delivering the discretionary insulin to the user comprises delivering the discretionary insulin in lieu of the non-discretionary insulin delivered according to the non-discretionary insulin delivery schedule.

4. The method of claim 1, wherein ceasing the discretionary insulin delivery mode of the system comprises ceasing the discretionary insulin delivery mode of the system responsive to the tracked discretionary insulin indicating that a complete dosing of the discretionary insulin has been delivered to the user.

5. The method of claim 1, wherein ceasing the discretionary insulin delivery mode of the system comprises ceasing the discretionary insulin delivery mode of the system responsive to the tracked discretionary insulin indicating that a maximum amount of the discretionary insulin according to the user input set of parameters has been delivered within a time period.

6. The method of claim 1, wherein ceasing the discretionary insulin delivery mode of the system comprises ceasing the discretionary insulin delivery mode of the system responsive to the received glucose value indicating that a desired glucose level has been achieved.

* * * * *